United States Patent [19]
Farbood et al.

[11] Patent Number: 5,837,659
[45] Date of Patent: Nov. 17, 1998

[54] PROCESS FOR PRODUCING $C_9$, $C_{11}$ AND $C_{13}$ ALKANOLS AND MICROORGANISM CAPABLE OF THE SAME

[75] Inventors: Mohamad I. Farbood, Holmdel; Laura E. Kizer, Sea Bright; Lynda B. McLean, Matawan; Mark A. Sprecker, Sea Bright, all of N.J.

[73] Assignee: International Flavors & Fragrances Inc., New York, N.Y.

[21] Appl. No.: 915,934

[22] Filed: Aug. 21, 1997

[51] Int. Cl.⁶ .............................. C11D 9/44; C11D 3/50; A61K 7/46
[52] U.S. Cl. ............................................. 510/101; 512/25
[58] Field of Search ................................ 512/25; 510/101

[56] References Cited

U.S. PATENT DOCUMENTS 4,168,248  9/1979  Kulka ........................................ 512/25

OTHER PUBLICATIONS

Caplus Abstract 1986:205560 Caplus Farbood et al EP 170243, Feb. 5, 1986.
Caplus Abstract 1993:427852 Caplus Naoshima et al J. Chem Soc. Perkin Trans 1 (1993), (5) 557–561.
Forney, et al I, Journal of Bacteriology, vol. 93, No. 2, Feb. 1967, pp. 649–655, entitled "Bacterial Oxidation of 2–Tridecanone to 1–Undecanol".

Forney, et al II, Biochemical and Biophysical Research Communications, vol. 37, No. 1, 1969, pp. 31–38, entitled "An Enzyme System for Aliphatic Methyl Ketone Oxidation".

*Primary Examiner*—Herbert J. Lilling
*Attorney, Agent, or Firm*—Arthur L. Liberman

[57] ABSTRACT

Described is a microbiological method for producing $C_9$, $C_{11}$, and $C_{13}$ alkanols defined according to the structures:

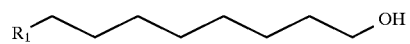

and

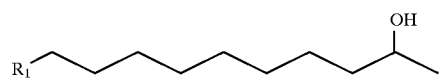

wherein $R_1$ is methyl or n-propyl using ketones defined according to the generic structure:

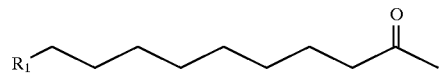

as a substrate and using the microorganism:

*Pseudomonas cepacia* ATCC 55792 or mutants thereof.

5 Claims, 9 Drawing Sheets

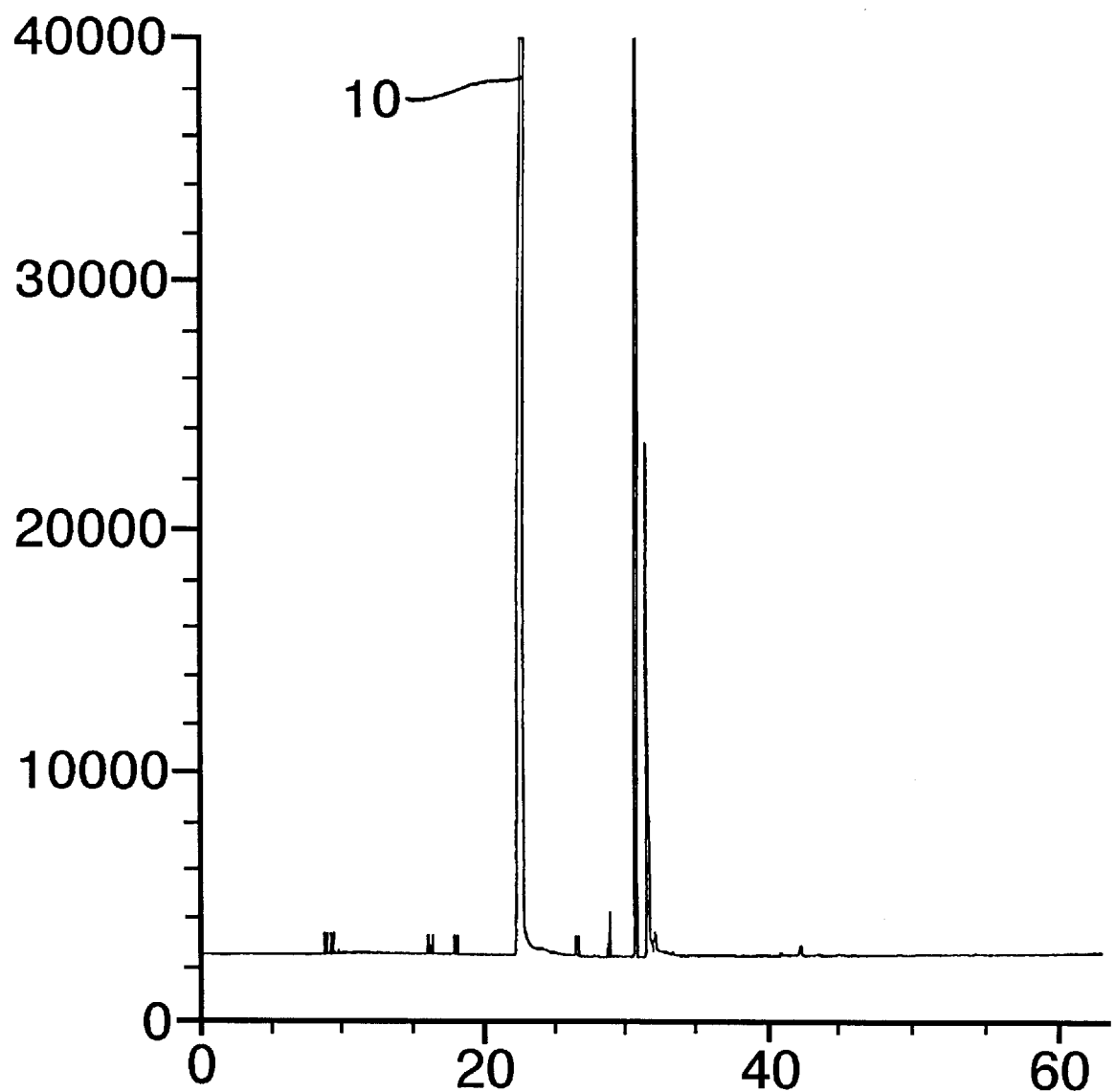
FIG. 1-A

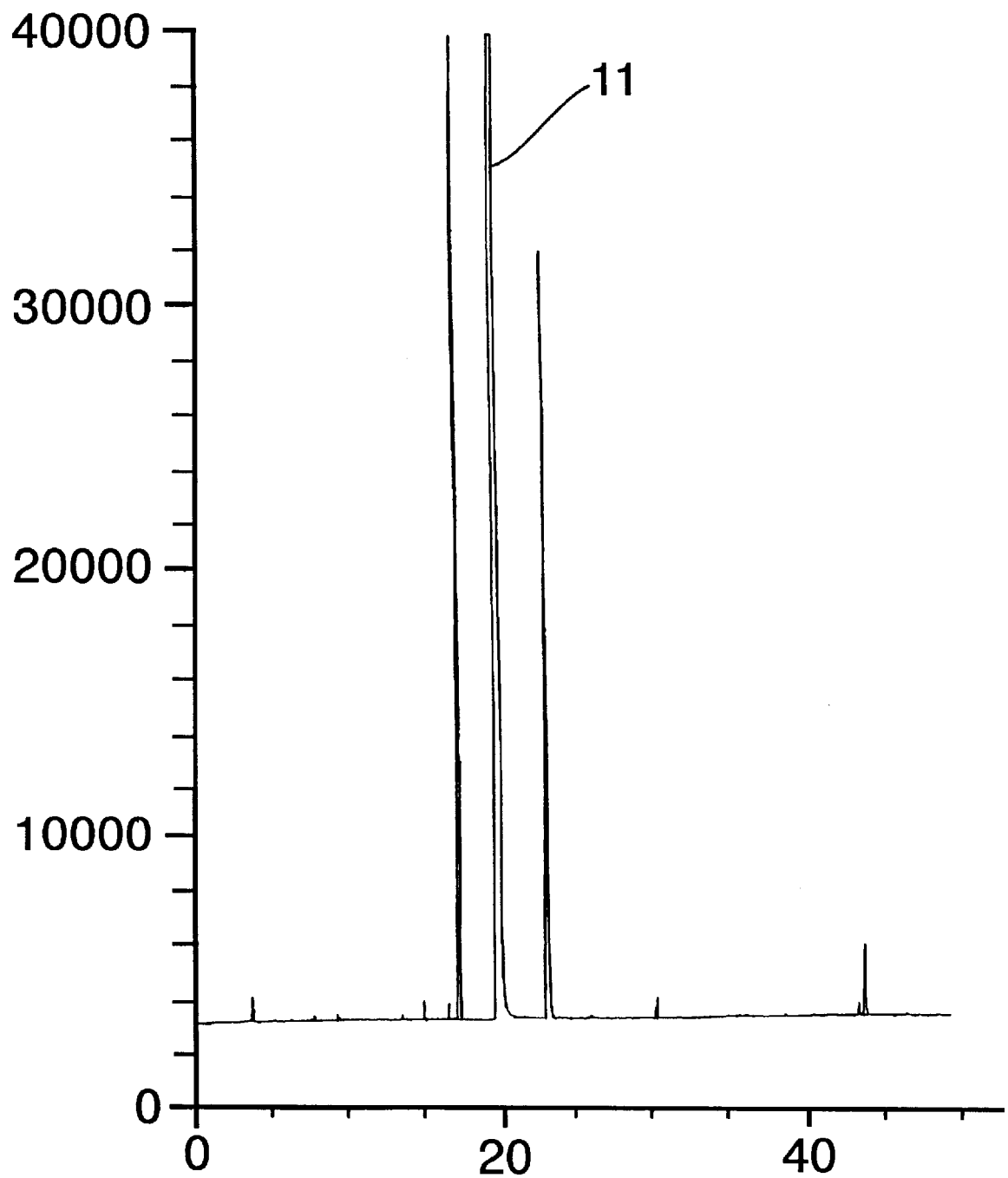
FIG. 1-B

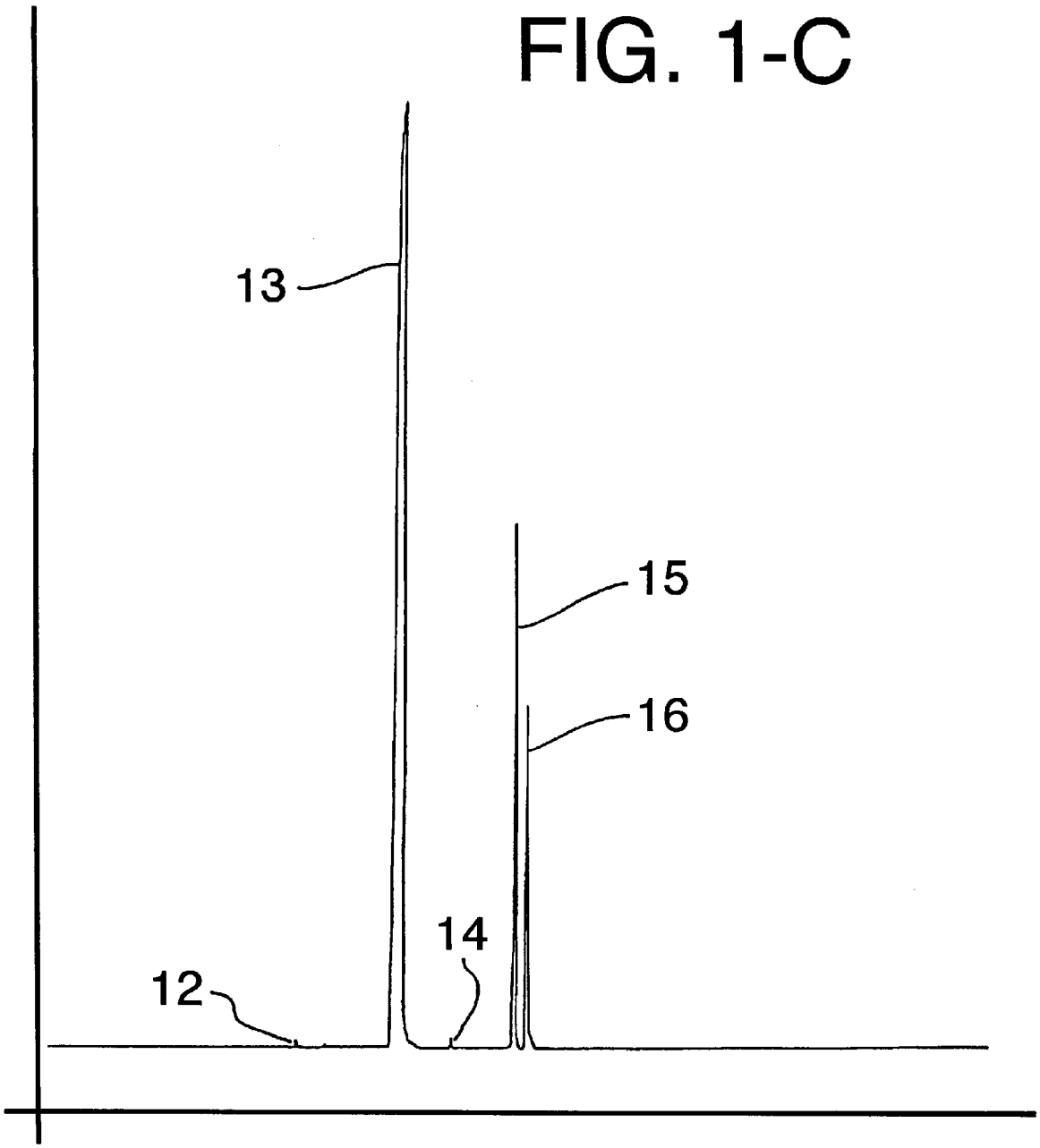
FIG. 1-C

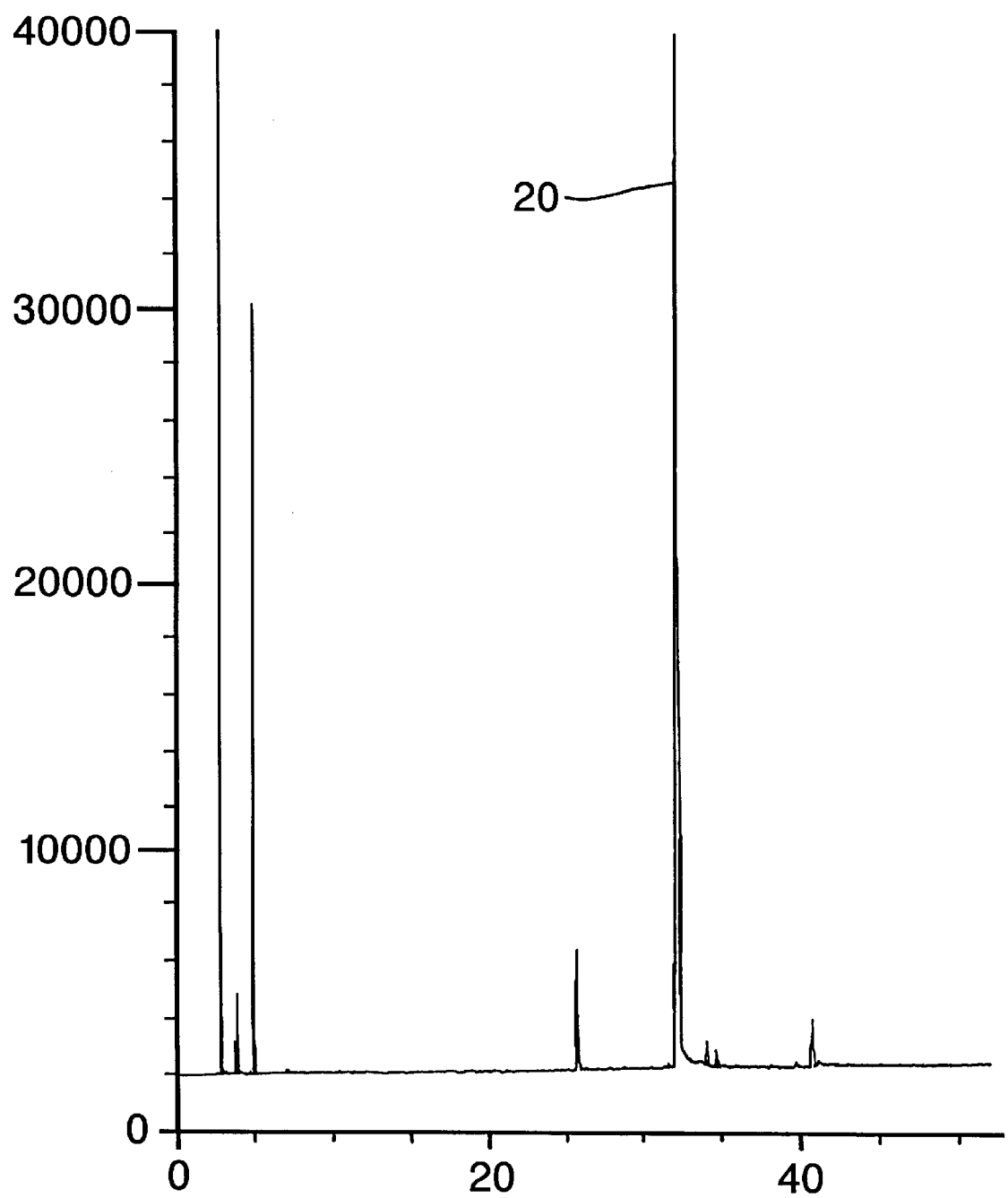
FIG. 2-A

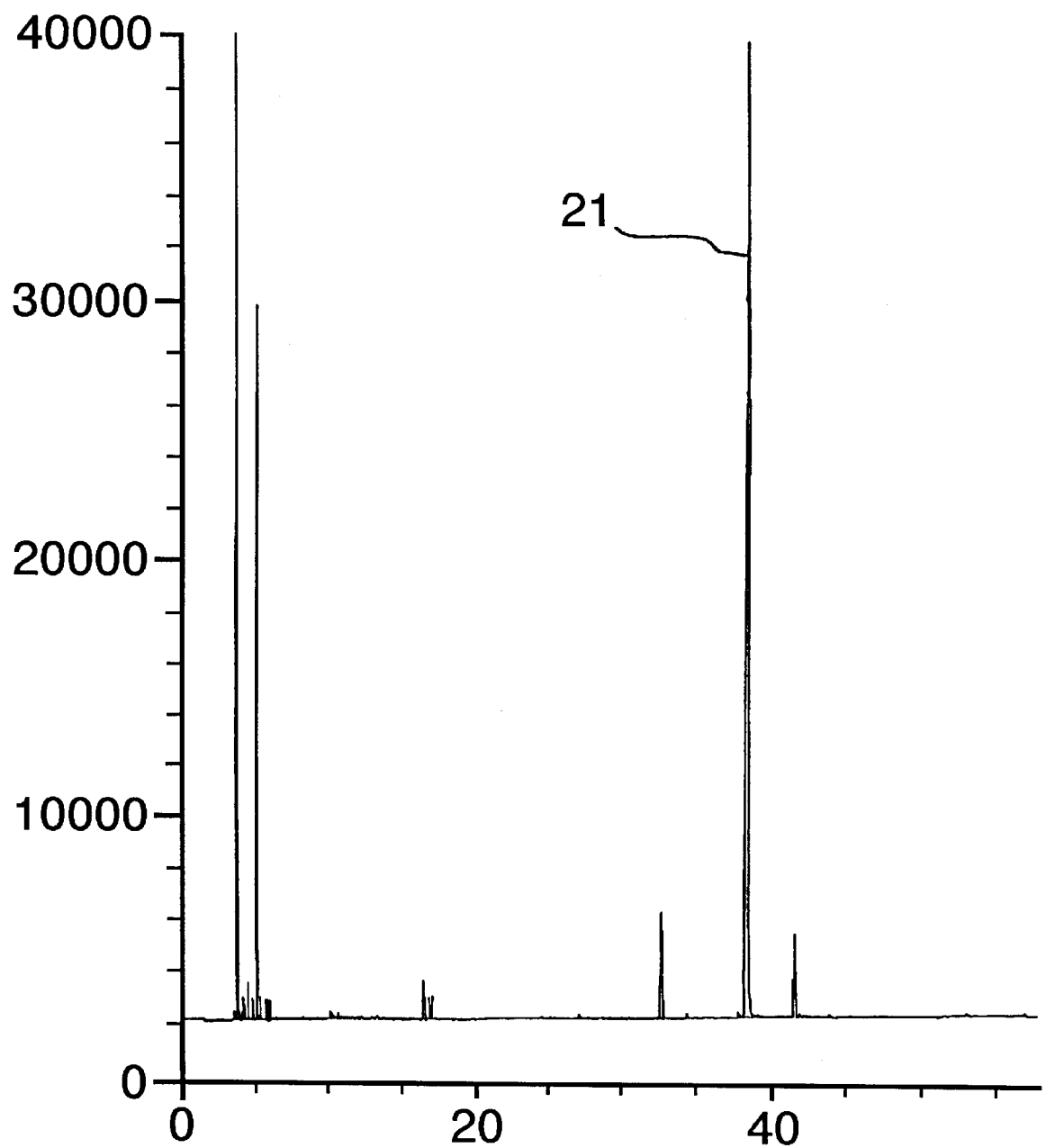

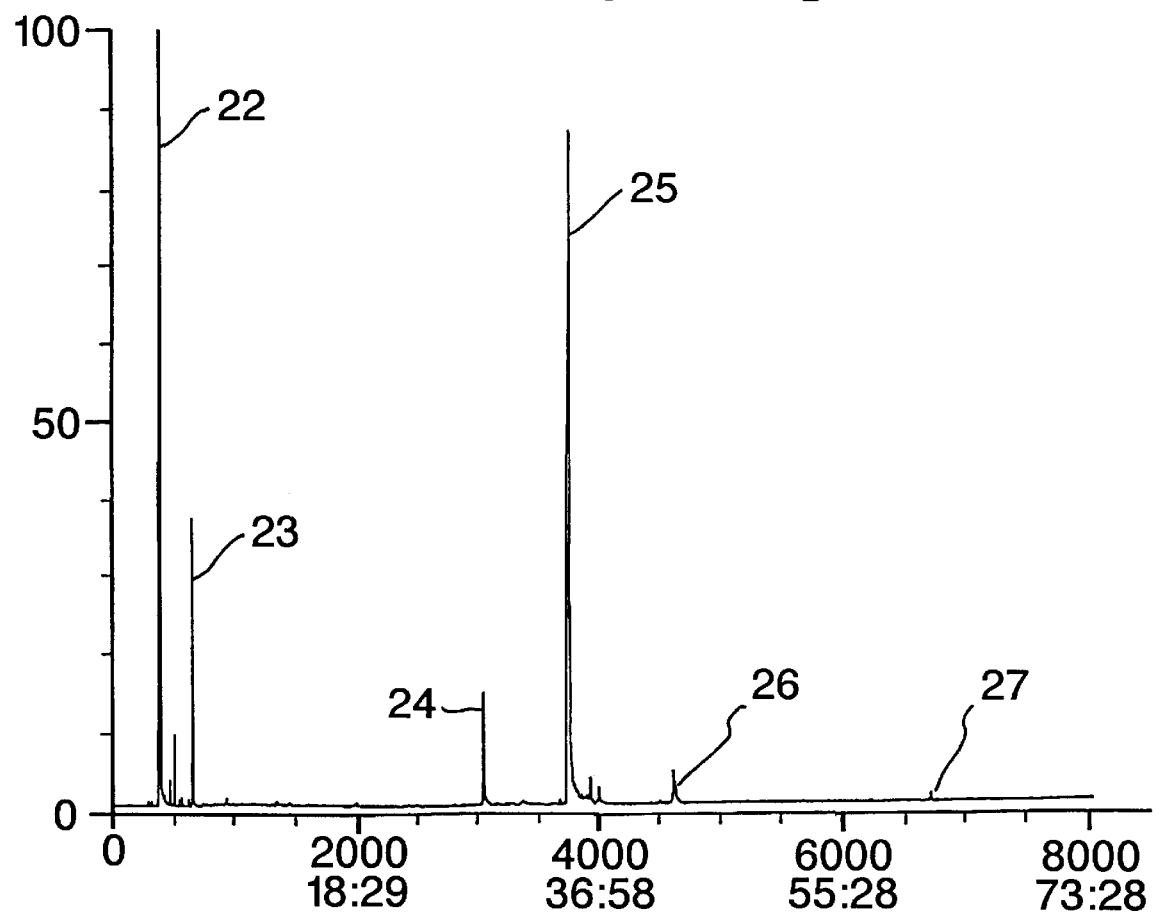
FIG. 2-C

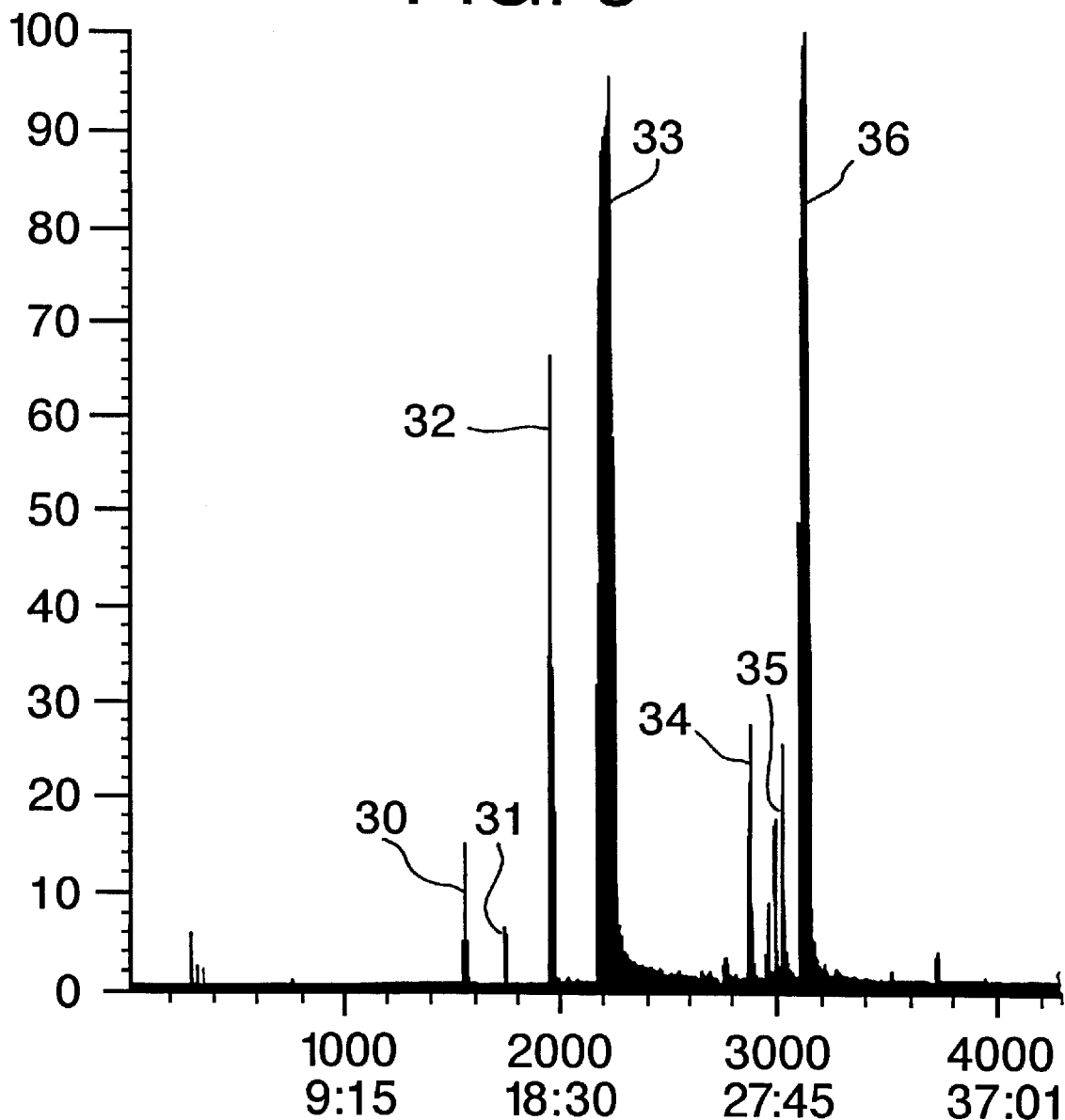

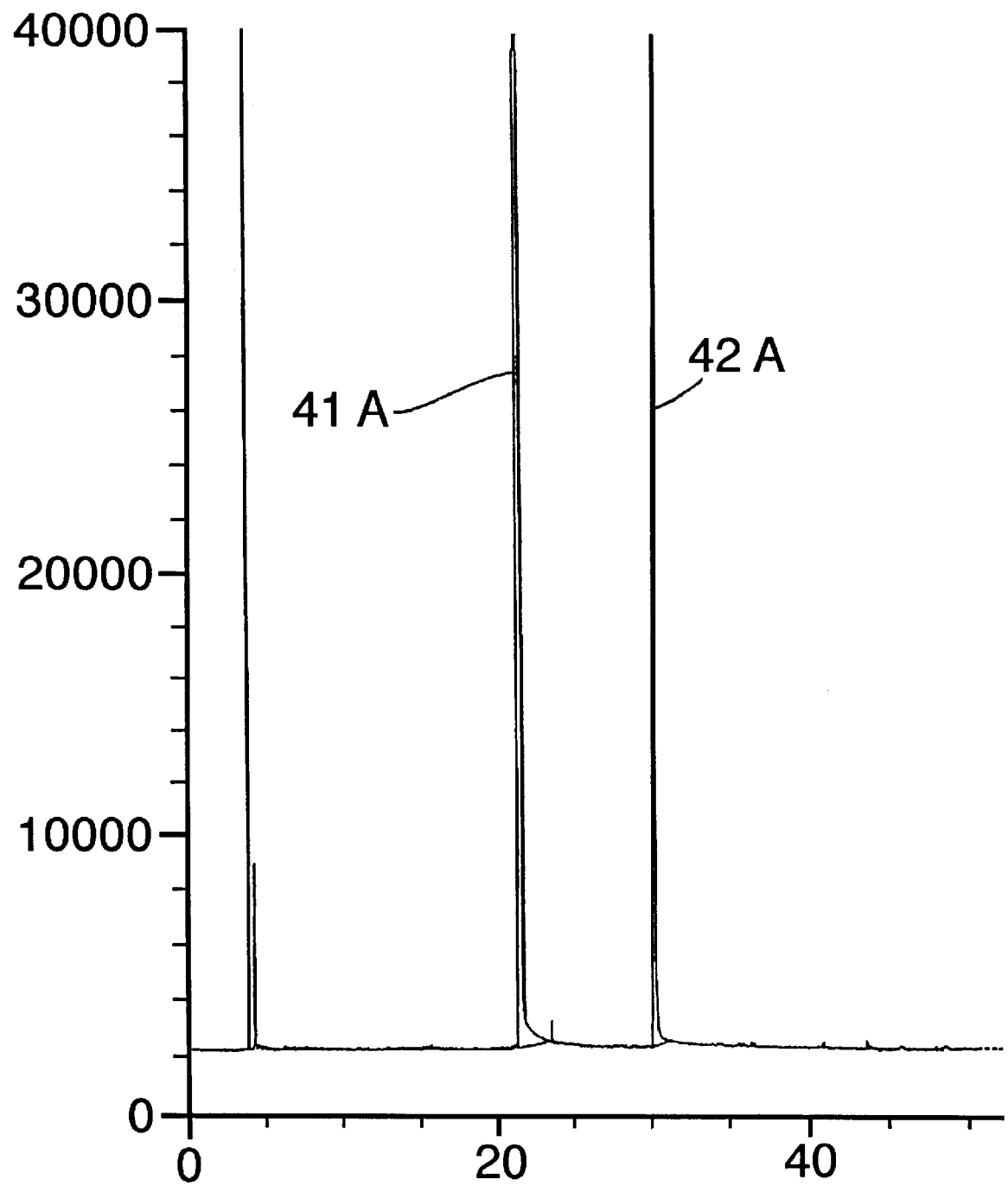
FIG. 4-A

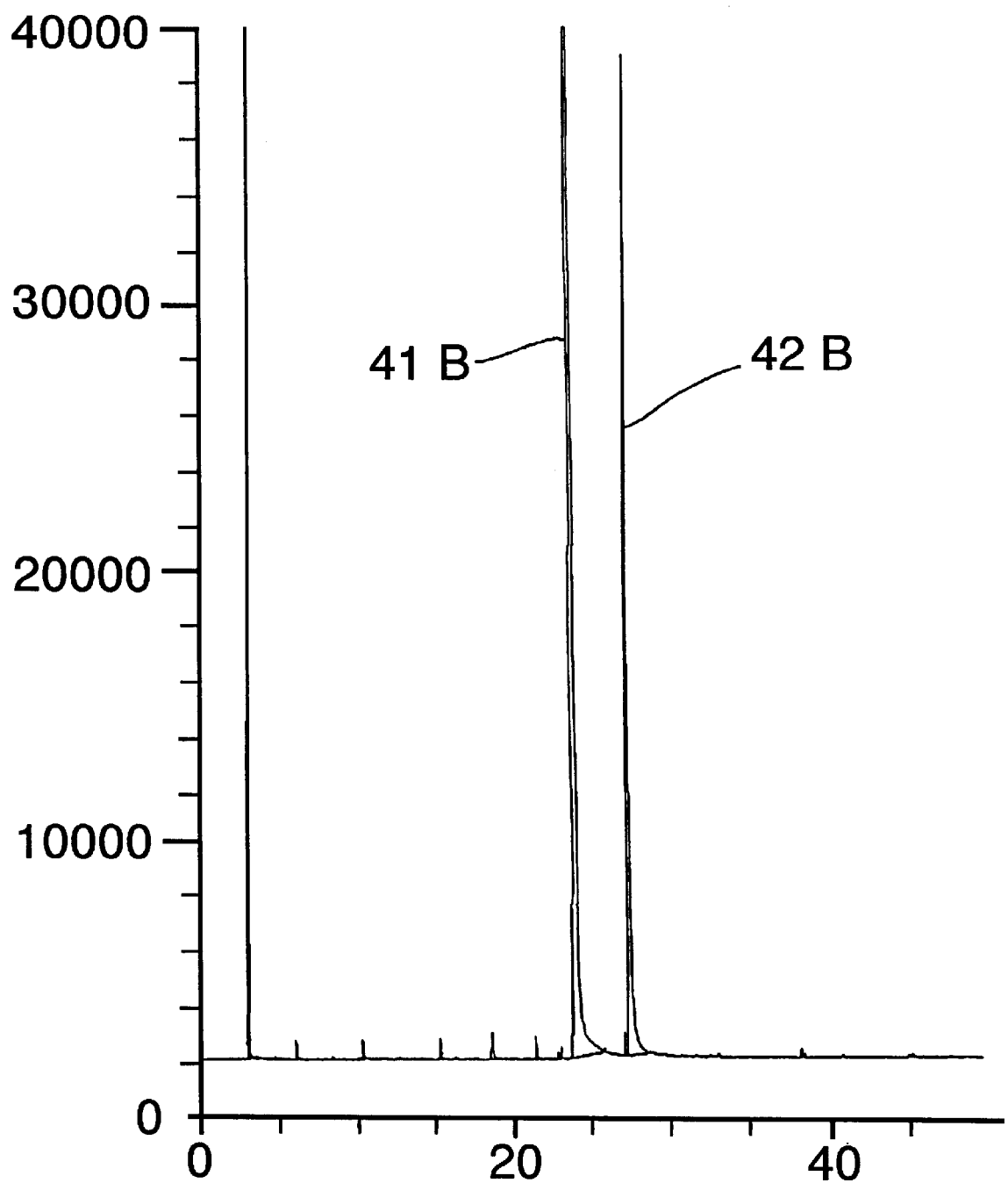

PROCESS FOR PRODUCING C₉, C₁₁ AND C₁₃ ALKANOLS AND MICROORGANISM CAPABLE OF THE SAME

BACKGROUND OF THE INVENTION

1-Nonanol having the structure:

2-undecanol having the structure:

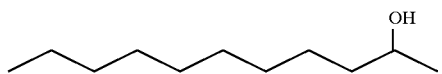

and 1-undecanol having the structure:

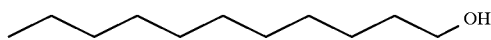

are each useful flavorants for foodstuffs. Thus, Arctander, *Perfume and Flavor Chemicals (Aroma Chemicals)*, Volume II, published in 1969 indicates at monograph 2348 that nonanol-1 having the structure:

has a "refreshingly citrusy-sweet taste" and that traces of this alcohol are used in flavor compositions, e.g., imitation butter, peach, pineapple, orange and other citrus types. At monograph 3031, Arctander indicates that undecanol-1 having the structure:

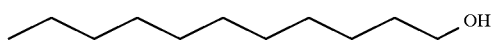

at concentrations below 20 ppm has a citrusy, oily-fruity, mildly sweet taste. Arctander indicates that both compounds having the structures:

and

are useful in perfume compositions.

*FENAROLI'S HANDBOOK of FLAVOR INGREDIENTS*, Second Edition, Volume 2, Furia and Bellanca, published by the CRC Press, Inc. indicates that 2-undecanol having the structure:

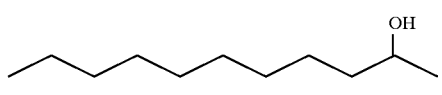

and stereoisomers thereof having the structures:

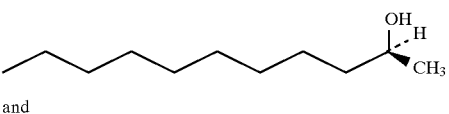

and

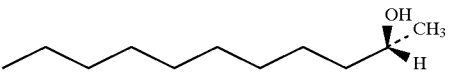

are useful at 20 ppm in baked goods flavors having a fatty odor with a fruity note and a fruity taste at low concentrations. Fenaroli's Handbook further indicates that the d-stereoisomer having an optical rotation of +10.29° occurs in coconut oil and the l-stereoisomer having an optical rotation of −1.18° is found in rue oil. Fenaroli's Handbook further states that the l-form of the optical isomer having an optical rotation of −5.40° is produced from *Litsea odorifera*.

Fenaroli's Handbook indicates that the 2-undecanol having the structure:

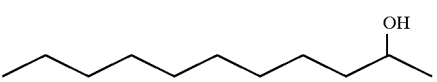

has an FEMA number of 3246 (Flavor Extracts Manufacturing Association). Arctander indicates that the compound having the structure:

has an FEMA number of 2789 and that the compound having the structure:

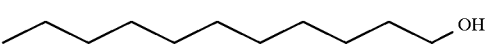

has an FEMA number of 3097.

Accordingly, a need has arisen for an efficaceous production of natural compounds having the structures:

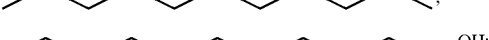

and, in addition, the d-stereoisomer having the structure:

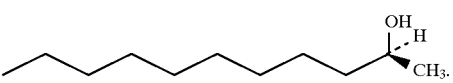

Forney and Markovetz, Volume 37, No. 1, 1969, *BIOCHEMICAL AND BIOPHYSICAL RESEARCH COMMUNICATIONS*, at pages 31–38, disclose the enzymatic conversion of 2-tridecanone to undecyl acetate using *Pseudomonas aeruginosa* according to the reaction sequence:

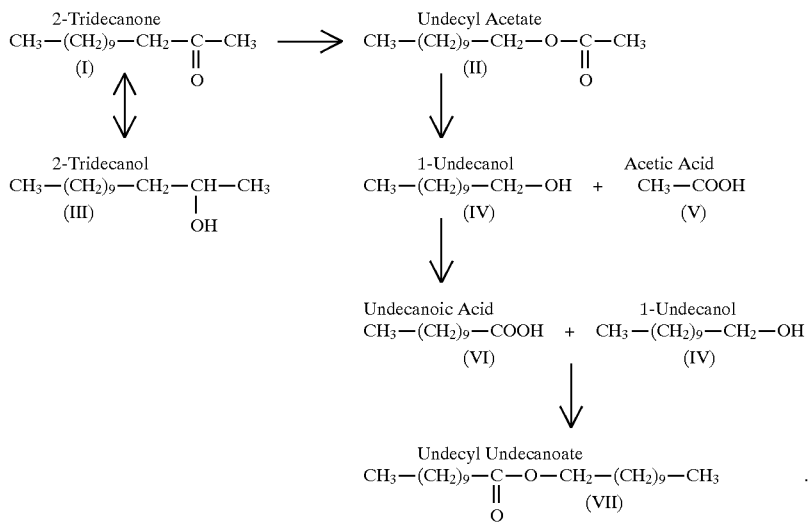

Forney, et al in the *JOURNAL Of BACTERIOLOGY*, February 1967 at pages 649–655, Volume 93, No. 2, entitled "Bacterial Oxidation of 2-Tridecanone to 1-Undecanol" using Pseudomonas 4G-9. Furthermore, Forney, et al discloses the growth of Pseudomonas 4G-9 on various substrates in Table 1 at page 652 as follows:

| "Growth of pseudomonas 4G-9 on various substrates | | |
|---|---|---|
| Substrate | Incubation days | Relative Growth[a] |
| 2-Heptanone | 12 | – |
| 2-Octanone | 12 | – |
| 2-Nonanone | 12 | ++++ |
| 2-Decanone | 12 | ++++ |
| 2-Undecanone | 12 | ++++ |
| n-Octane | 12 | – |
| n-Nonane | 12 | ++ |
| n-Decane | 12 | + |
| n-Undecane | 12 | ++ |
| n-Dodecane | 12 | +++ |
| n-Tridecane | 12 | ++++ |
| Nonanoate[b] | 5 | ++ |
| Decanoate | 5 | +++ |
| Undecanoate | 5 | ++++ |
| Dodecanoate | 5 | ++++ |
| 1-Nonanol | 5 | – |
| 1-Decanol | 5 | ++++ |
| 1-Undecanol | 5 | ++++ |
| 1-Dodecanol | 5 | ++++ |
| 1,2-Dodecanediol[b] | 21 | – |
| 1,2-Tetradecanediol | 21 | ++++ |

[a]Symbols: –, no growth; +, slight growth; ++, moderate growth; +++, abundant growth; ++++, maximal growth.
[b]Substrates used at 0.1% concentration (w/v)."

Nothing, however, in the prior art discloses a process for producing a mixture of alkanols defined according to the structures:

and

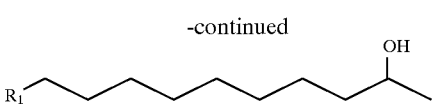

containing at least 65 mole percent of the alkanol defined according to the structure:

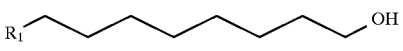

in a high yield. Nothing in the prior art shows the use of such an organism as *Pseudomonas cepacia* ATCC 55792 in effecting such production of a mixture of alkanols defined according to the structures:

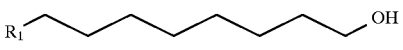

and

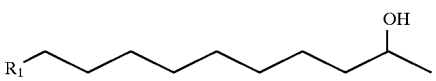

(wherein $R_1$ represents methyl or n-propyl)

BRIEF DESCRIPTION OF THE DRAWINGS

FIG. 1A is the GC-capillary survey for the reaction product of Example I containing the compounds having the structures:

and

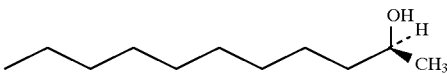

(conditions: 50 meter×0.32 mm×0.5 micrometer methyl silicon (OV-1) column programmed from 75–225° C. at 2° C. per minute).

FIG. 1B is a GC-capillary survey for the reaction product of Example I containing the compounds having the structures:

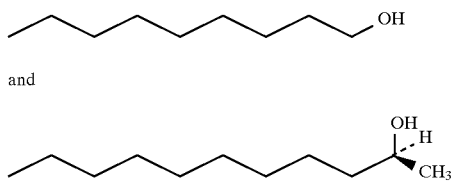

and (conditions: 50 meter×0.32 mm×0.3 mm CARBOWAX® 20M column programmed from 75–225° C. at 2° C. per minute).

FIG. 1C is the total ion chromatogram for the reaction product of Example I containing the compounds having the structures:

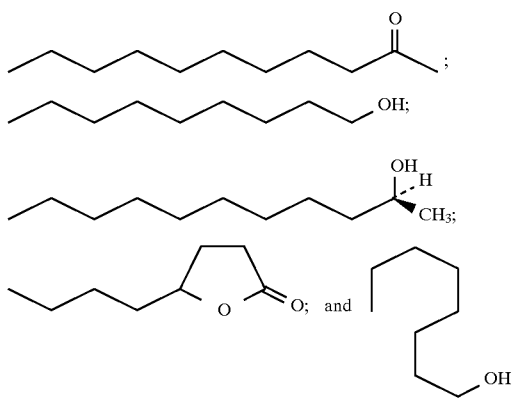

(conditions: methyl silicon (OV-1) column programmed from 75–225° C. at 2° C. per minute).

FIG. 2A is a GC-capillary survey for the reaction product of Example XVII containing the compounds having the structures:

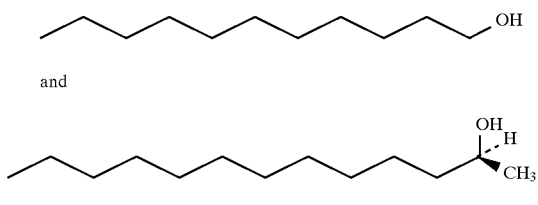

(conditions: 50 meter×0.32 mm×0.5 micrometers methyl silicon (OV-1) column programmed from 75–225° C. at 2° C. per minute).

FIG. 2B is a GC-capillary survey for the reaction product of Example XVII containing the compounds having the structures:

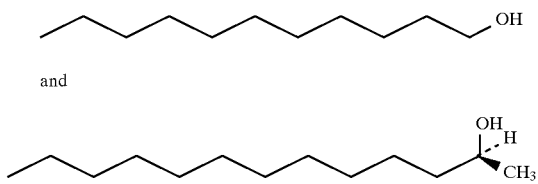

(conditions: 50 meter×0.32 mm×0.3 micrometers CARBOWAX® 20M column programmed from 75–225° C. at 2° C. per minute).

FIG. 2C is a total ion chromatogram for the reaction product of Example XVII containing the compounds having the structures:

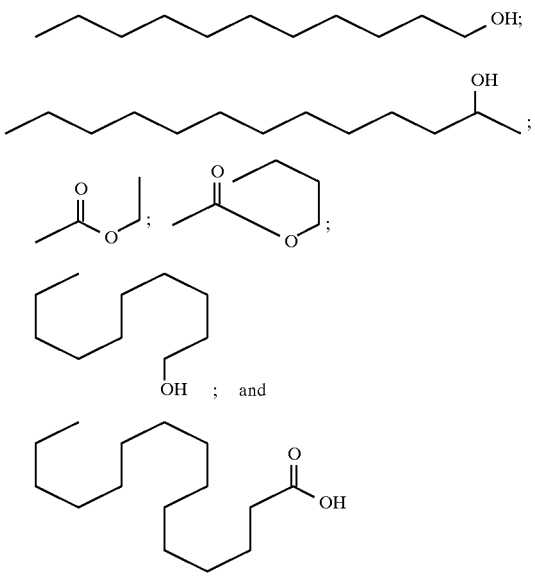

(conditions: OV-1 (methyl silicon) column programmed from 75–225° C. at 2° C. per minute).

FIG. 3 is a total ion chromatogram for the crude product of Example XVIII containing the compounds having the structures:

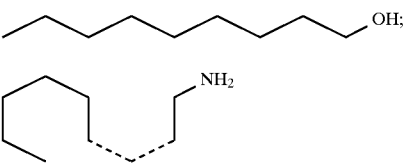

(representing a mixture of compounds wherein in the mixture, one of the dashed lines represents a carbon carbon single bond and the other of the dashed lines represents represents a carbon carbon double bond);

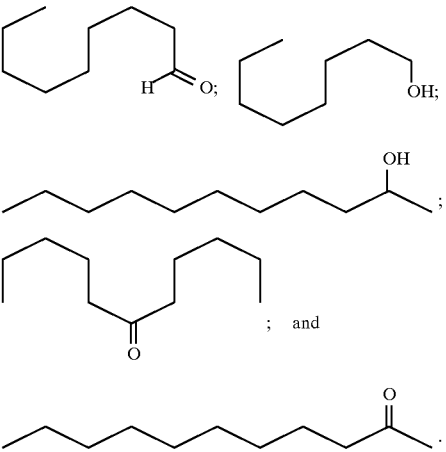

FIG. 4A is a GC-capillary survey for the purified product of Example XVIII containing the compounds having the structures:

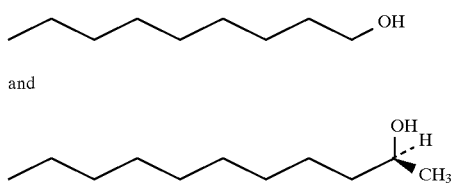

and

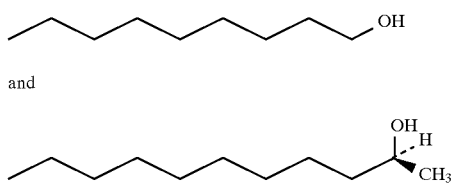

(conditions: 50 meter×0.32 mm×0.5 micrometers methyl silicon (OV-1) column programmed from 75–225° C. at 2° C. per minute).

FIG. 4B is a GC-capillary survey for the purified product of Example XVIII containing the compounds having the structures:

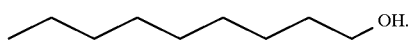

and

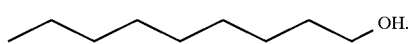

(conditions: 50 meter×0.32 mm×0.5 micrometers CARBOWAX® 20M column programmed from 75–225° C. at 2° C. per minute).

DETAILED DESCRIPTION OF THE DRAWINGS

Referring to FIG. 1A, the GC-capillary survey for the product of Example I, the peak indicated by reference numeral 10 is for the compound having the structure:

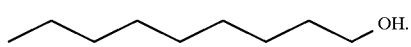

Referring to FIG. 1B, the GC-capillary survey for the product of Example I, the peak indicated by reference numeral 11 is for the compound having the structure:

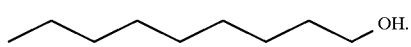

Referring to FIG. 1C, the total ion chromatogram for the reaction product of Example I, the peak indicated by reference numeral 12 is for the compound having the structure:

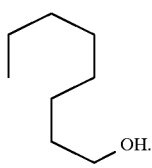

The peak indicated by reference numeral 13 is for the compound having the structure:

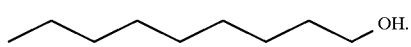

The peak indicated by reference numeral 14 is for the compound having the structure:

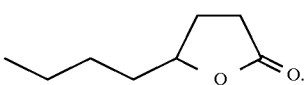

The peak indicated by reference numeral 15 is for the compound having the structure:

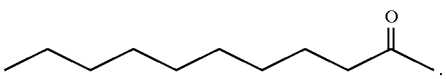

The peak indicated by reference numeral 16 is for the compound having the structure:

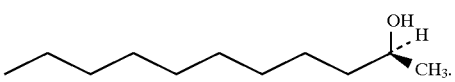

Referring to FIG. 2A, the GC-capillary survey for the reaction product of Example XVII, the peak indicated by reference numeral 20 is for the compound having the structure:

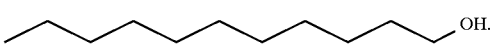

Referring to FIG. 2B, the GC-capillary survey for the reaction product of Example XVII, the peak indicated by reference numeral 21 is for the compound having the structure:

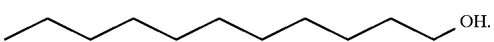

Referring to FIG. 2C, the total ion chromatogram for the reaction product of Example XVII, the peak indicated by reference numeral 22 is for the compound having the structure:

The peak indicated by reference numeral 23 is for the compound having the structure:

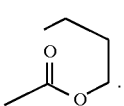

The peak indicated by reference numeral 24 is for the compound having the structure:

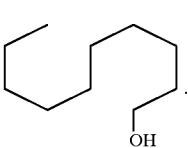

The peak indicated by reference numeral 25 is for the compound having the structure:

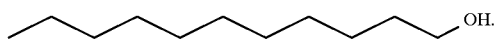

The peak indicated by reference numeral 26 is for the compound having the structure:

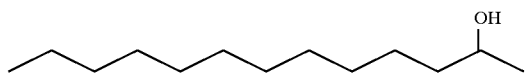

The peak indicated by reference numeral 27 is for the compound having the structure:

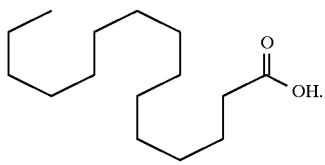

Referring to FIG. 3, the total ion chromatogram for the crude product of Example XVIII, the peak indicated by reference numeral 30 is for the compound having the structure:

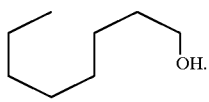

The peak indicated by reference numeral 31 is for the compound having the structure:

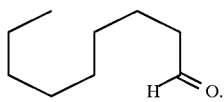

The peak indicated by reference numeral 32 is for the mixture of compounds defined according to the structure:

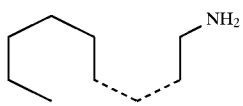

wherein in the mixture in one of the compounds, one of the dashed lines is a carbon carbon double bond and the other of the dashed lines is a carbon carbon single bond. The peak indicated by reference numeral 33 is for the compound having the structure:

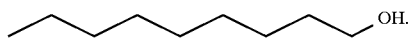

The peak indicated by reference numeral 34 is for the compound having the structure:

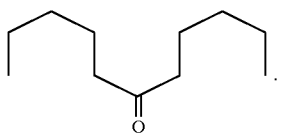

The peak indicated by reference numeral 35 is for the compound having the structure:

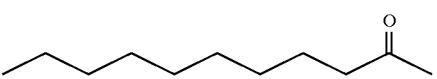

The peak indicated by reference numeral 36 is for the compound having the structure:

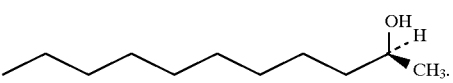

Referring to FIG. 4A, the GC-capillary survey for the purified product of Example XVIII, the peak indicated by reference numeral 41A is for the compound having the struture:

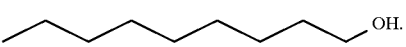

The peak indicated by reference numeral 42A is for the compound having the structure:

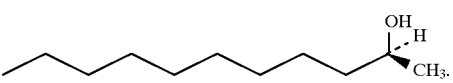

Referring to FIG. 4B, the GC-capillary survey for the purified product of Example XVIII, the peak indicated by reference numeral 41B is for the compound having the structure:

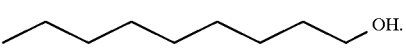

The peak indicated by reference numeral 42B is for the compound having the structure:

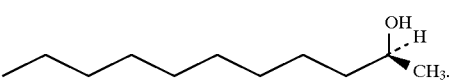

SUMMARY OF THE INVENTION

The present invention concerns biologically pure cultures of the microorganism:

*Pseudomonas cepacia* ATCC 55792 capable of producing in high yields with high conversions at least one mixture of alkanols containing the compounds defined according to the generic structures:

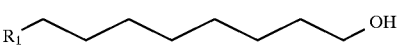

and

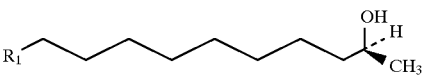

(the mixture having an optical rotation of between about +0.2 and about +0.9° due to the presence of optical isomers defined according to the structure:

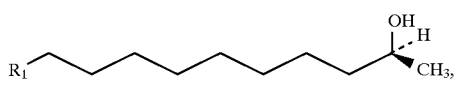

with the major proportion of the composition being those compounds defined according to the structure:

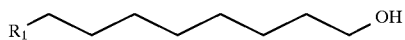

and with compounds defined according to the structure:

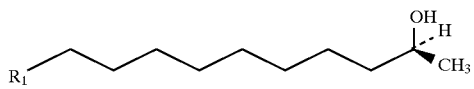

being optical isomers having optical rotations of between about +3 and about +4° under aerobic conditions and in an aqueous medium containing at least one ketone defined according to the generic structure:

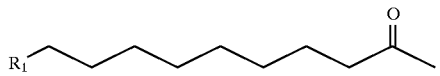

wherein $R_1$ is methyl or n-propyl.

In carrying out the reaction using *Pseudomonas cepacia* ATCC 55792 (or a mutant thereof), the following reaction takes place:

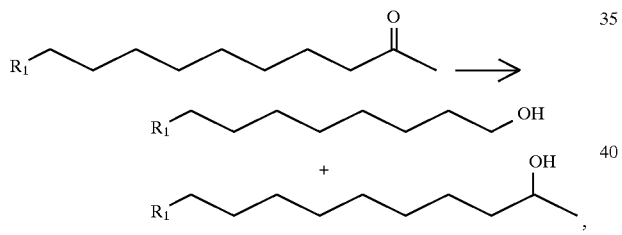

more specifically, shown thusly:

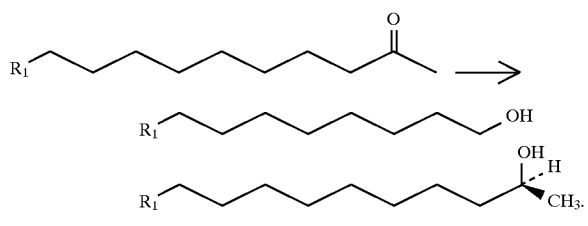

By way of example, our invention contemplates processes defined by the following reactions:

(1) using *Pseudomonas cepacia* ATCC 55792 (or a mutant thereof):

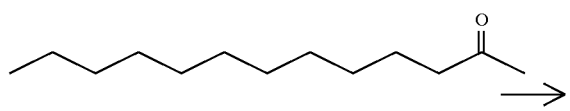

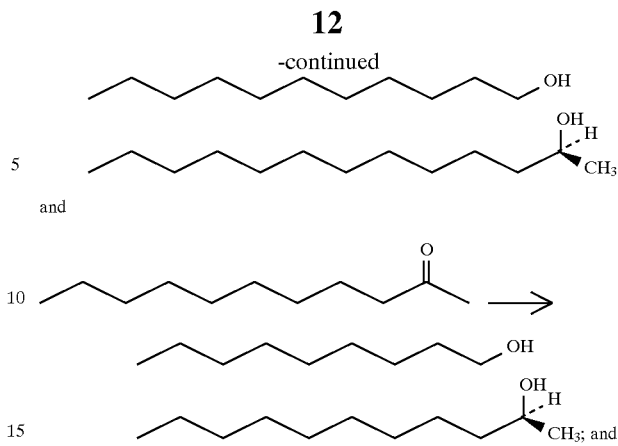

and

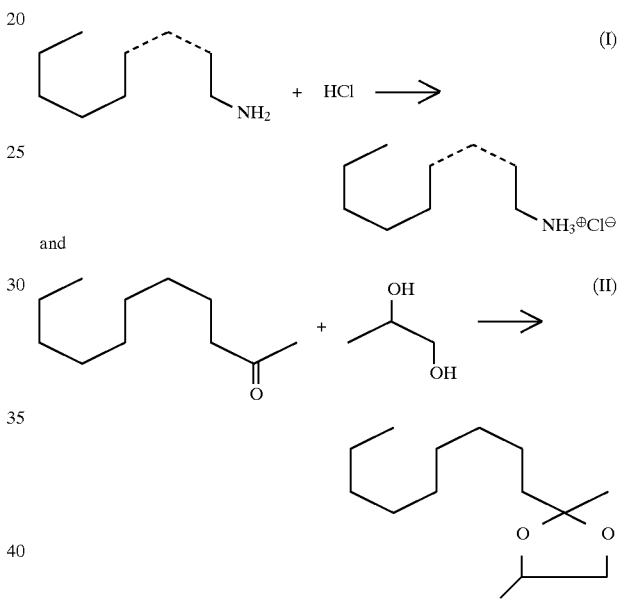

(2) purification reactions for purification of the resulting products:

In view of the impurities contained in the resulting crude reaction products:

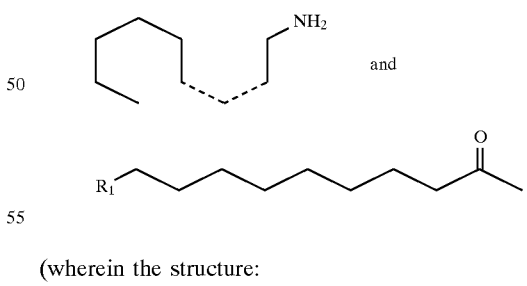

(wherein the structure:

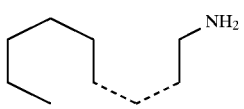

represents a mixture and in the mixture one of the dashed lines represents a carbon carbon double bond and the other of the dashed lines represents a carbon carbon single bond).

The structures shown thusly herein:

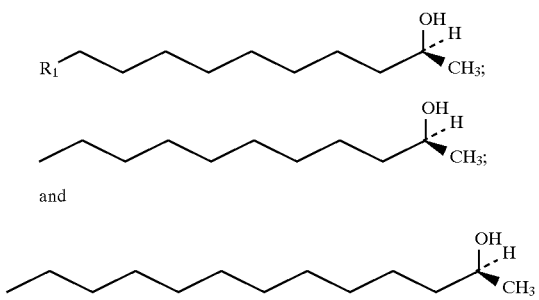

are for the "dextrorotatory(+)" optical isomers of the compounds having the structures:

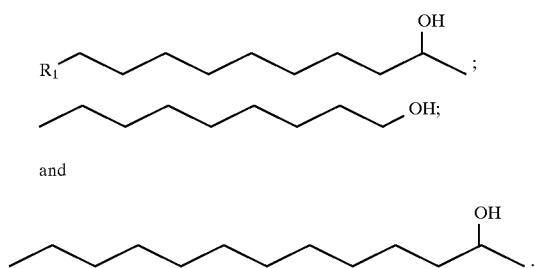

The form in which the microorganism is used is not critical. It can be used as the culture (suspension), i.e., including the cells and the corresponding nutrient solution, or in the form of cells suspended in a buffer solution. The cells, or an enzyme extract thereof, may be immobilized on a suitable solid support, which may then be used to effect transformations.

The suspended culture mixture is prepared by inoculation of a suitable aqueous nutrient medium with the microorganism (or a mutant thereof). A suitable nutrient medium is one which contains nitrogen sources, inorganic salts, growth factors, the desired substrate(s) and, optionally, other carbon sources. Some carbon sources suitable for use in the inventive process include, for example, glucose, galactose, L-sorbose, maltose, sucrose, cellobiose, trehalose, L-arabinose, L-rhamnose, ethanol, glycerol, L-erythrithol, D-mannitol, lactose, melibiose, raffinose, melezitose, starch, D-xylose, D-sorbitol, α-methyl-D-glucoside, lactic acid, citric acid and succinic acid. Suitable nitrogen sources include, for example, nitrogen-containing organic substances such as peptone, meat extract, yeast extract, corn steep liquor, casein, urea, amino acids, or nitrogen-containing inorganic compounds such as nitrates, nitrites and inorganic ammonium salts. Suitable inorganic salts include, for example, phosphates of magnesium, potassium, calcium or sodium. The above-mentioned culture medium nutrients may be supplemented with, for example, one or more vitamins of the B group and/or one or more trace minerals such as Fe, Mo, Cu, Mn and B, as desired. The vitamins of trace minerals are not necessary when a small amount of yeast extract is added to the medium. Addition of an antibiotic, such as chloroamphenicol or chlorotetracycline, may be desirable when bacterial contamination is a problem.

The cultivation of the microorganism may be carried out as a stationary culture or as a submersed (e.g., shaking culture, fermentation culture) under aerobic conditions. One may suitably work in the pH range of from between 2.5 and about 9.0 and preferably in the range of between about 3.0 and about 7.5 and most preferably between about 3.0 and about 6.5. The pH may be regulated by the addition of inorganic or organic acids such as hydrochloric acid, acetic acid and oxalic acid, or by the addition of bases such as sodium hydroxide and ammonium hydroxide, or by the addition of a buffer such as a phosphate or a phthalate. The incubation temperature should suitably be maintained between about 12° C. and about 33° C., with a range between about 15° C. and about 30° C. being more preferred, and a range between about 18° C. and about 28° C. being most preferred.

The process according to this invention may be conveniently carried out by adding one or a mixture of the ketones having the structure:

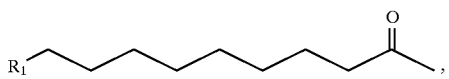

to the nutrient medium at the onset of cultivation as the sole carbon source. Alternatively, the substrate may be added in combination with another carbon source, such as dextrose, either during cultivation or when the carbon source is depleted. The only restriction on the concentration of substrate in the culture medium is that of being able to effectively aerate the culture. However, the substrate concentration is preferably in the range of between about 0.1 g/L and about 100 g/L, more preferably in the range of between about 0.5 g/L and about 50 g/L, and most preferably in the range of between about 2.5 g/L and about 30 g/L. The transformation can be suitably carried out under any of the above-mentioned conditions.

The total transformation time (after initial cultivation period) may vary depending on the composition of the nutrient medium and the substrate concentration. In general, shaking flask cultures require from between about 12 hours and about 264 hours. However, when a fementor is used, the cultivation time may be reduced to about 48 hours or less.

Additional conditions of the transformation as shown by the reaction:

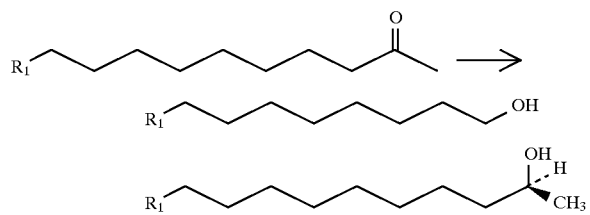

are:
(a) a temperature in the range of from about 20° C. up to about 45° C., preferably from about 25° C. up to about 40° C., and most preferably from about 25° C. up to 30° C. at a pressure of from about zero psig (atmospheric) up to about 15 psig;
(b) a pH range of from about 5.0 up to about 8.5, preferably from about 6.0 up to about 8.0, and most preferably from about 6.5 up to about 7.5; and
(c) an aeration range of from about 0.1 up to about 1.5 v/v/m of air at 1 atmosphere pressure (liter per liter per minute).

The transformation may be carried out using the cells of the microorganism isolated from the culture solution, with an enzyme extract isolated from the cells in a manner well known to the art. In this case, the transformation can be conveniently carried out in a variety of aqueous nutrient mediums including, for example, in a buffer solution, in a physiological salt solution, in a fresh nutrient solution or in water. The isolated cells or enzyme extract may be immobilized on a solid support and the desired transformation effected. Also, transformation of the substrate may be effected by mutants of this organism. Such mutants can be readily obtained by methods well known in the art, for example, by exposing the cells to UV or X-rays, or known mutagenic substances such as, for example, acridine orange, and are readily obtained as will be seen from Example I-M, infra The substrate can be added to the medium as a powder, or a slurry in an emulsifier such as TWEEN® 80 (polyoxyethylene-sorbitan monostearate), or as a solution in an emulsifier, or as a solution in a hydrophilic solvent such as acetone, methanol, ethanol, ethylene glycol, propylene glycol or dioxan. A surface-active agent or a dispersion agent can also be added to an aqueous suspension of the substrate, or the substrate can be emulsified using ultrasound.

Conventional antifoam agents, such as silicone oils (e.g., UCON®), polyalkyleneglycol derivatives, maize oil or soya oil, can be used to control foaming.

The transformation of the substrate can be monitored using standard analytical techniques such as GLC, TLC, HPLC, IR and NMR. If a rapid disappearance of the substrate is observed, more substrate can then be added in order to maximize the transformation capacity of the microorganism. The process is generally terminated when most of the substrate has disappeared from the culture medium. The compounds having the structures:

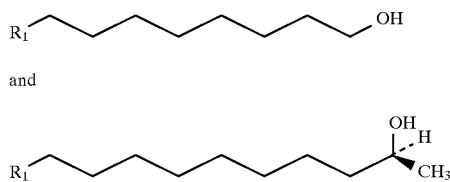

and

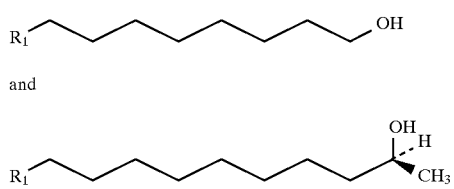

may be recovered from the aqueous nutrient medium as set forth in the Examples, infra, and as set forth below.

Isolation and purification of the compounds defined according to the structures:

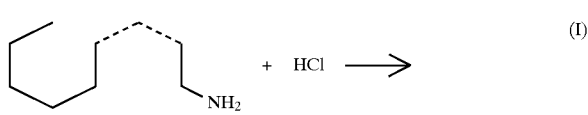

from the fermentation broths may be achieved by initially using conventional techniques including filtration or centrifugation, solvent extraction, distillation, crystallization and the like, and then carrying out a further purification (as exemplified in Example XVIII, infra) using, for example, the reactions:

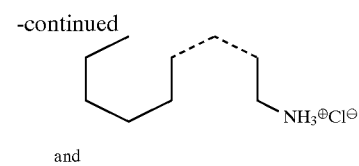

(I)

-continued

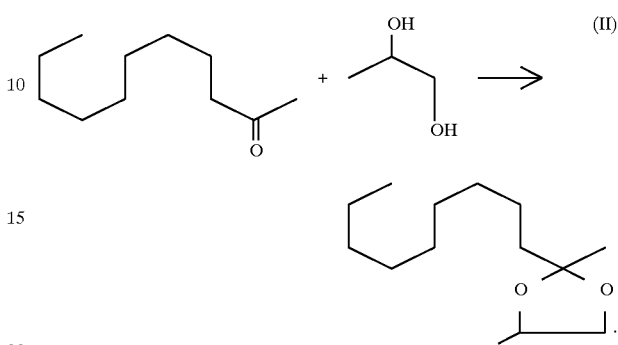

(II)

The mixture of compounds as defined according to the structures:

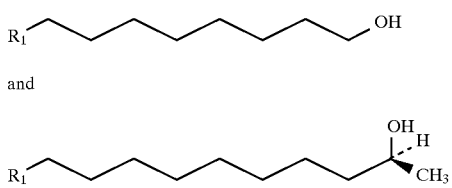

may be used for their organoleptic (flavor or fragrance) properties "as is" or they may be further distilled.

The microorganism employed in this invention was isolated form a soil sample obtained from central New Jersey, the United States of America. The strain has been deposited on June 7, 1996 with the American Type Culture Collection with the accession number as follows:

*Pseudomonas cepacia* ATCC 55792
(initially submitted to the American Type Culture Collection as IFF-8296C)

The address of the American Type Culture Collection is:
10801 University Blvd.
Manassas, Virginia
20110-2209
Telephone: 1-703-365-2700
Fax: 1-703-365-2750.

This isolate is a member of the Pseudomonas RNA Group II. The principal feature shared by the species in this group is nutritional versatility in the type and number of organic compounds utilized as sole sources of carbon and energy, which include carbohydrates, mono- and dicarboxylic acids, mono- and polyalcohols, aromatic compounds, amino acids and amines. The most outstanding property of RNA Group II is the fact that, with the exception of *Pseudomonas pickettii,* the species included are animal or plant pathogens [*Bergey's Manual of Systematic Bacteriology*, Volume 1, N.R. Krieg (ed.), Williams & Wilkins, 1984.] Growth occurs in mineral base medium containing ammonium ions as sole source of nitrogen and glucose as sole source of carbon and energy. A few strains fail to produce indophenol oxidase, and others produce a slow and very weak indolphenol oxidase reaction. The majority of the strains are not susceptible to antibiotics of the polymyxin class.

*Pseudomonas cepacia* was first described as a phytopathogen that causes sour skin, an onion bulb rot. It has wide geographic distribution and has been isolated from raw and pasteurized milk; hard lens and soft lens wetting and saline solutions; nasal sprays; rotting tree trunk; forest soil, muck soil; soil enrichments; and natural river and tap waters. *Pseudomonas cepacia* has also been isolated from a variety of clinical materials. It is an opportunistic pathogen, and most infections are of nosocomial origin. *Pseudomonas cepacia* demonstrates a multiple antibiotic resistance pattern, especially to the aminoglycosides usually active against *Pseudomonas aeruginosa*. *Pseudomonas cepacia* produce pathological changes in animals similar to those produced by *Pseudomonas pseudomallei* [G. L. Gilardi, 1985. *Pseudomonas*, pages 361–362.In E. H. Lennette, A. Balows, W. J. Hausler, Jr., and H. J. Shadomy (ed.), *Manual of Clinical Microbiology*, 4th edition, American Society for Microbiology, Washington, D.C.].

Strain exhibits the minimal characters for the identification of *Pseudomonas cepacia* strains (see Table I). Strain is identified as *Pseudomonas cepacia*.

Morphology:

This strain is a gram-negative; short rod. Cells occur singly and in pairs. It is motile by means of a tuft of polar flagella [lophotrichous, that is, three or more flagella]. In nitrogen deficient medium, cells accumulate poly-β-hydroxybutyrate as a carbon reserve material; this is a typical feature of *Pseudomonas cepacia*. Colonies showed the following characteristics in nutrient medium (ATCC medium #3):

Circular, entire margin smooth, glistening; convex elevation and butyrous in consistency. Strain did not have any pigmentation.

R. Y. Stanier, N. J. Palleroni and M. Doudoroff in their study of 19 strains of *Pseudomonas cepacia* found 2 strains which were completely non-pigmented [R. Y. Stanier, N. J. Palleroni and M. Doudoroff, 1966. "The Aerobic Pseudomonads: A Taxonomic Study," *J. Gen. Microbiol.*, 43:247–253]. Many strains of clinical origin are non-pigmented [G. L. Gilardi, 1985. *Pseudomonas*, page 361. In E. H. Lennette, A. Balows, W. J. Hausler, Jr. and H. J. Shadomy (ed.), *Manual of Clinical Microbiology*, 4th edition, American Society for Microbiology, Washington, D.C.]. Pigmentation is not correlated with any other phenotypic characters studied and, therefore, seem to be devoid of taxonomic significance.

Biochemical and Physiological Properties:

IFF-8296C is oxidase and catalase positive. Gelatin and starch are not hydrolyzed. Caesin is hydrolyzed and gave a positive lecithinase (egg yolk) reaction. Strain grows on MacConkey agar, but not on 0.05% centrimide agar. Denitrification is negative; nitrate is reduced to nitrite. Growth occurs at 42° C., 37° C., 30° C., 26° C., but not at 4° C. Metabolism is by respiration (aerobic). Strain is lipolytic [TWEEN® 80 hydrolysis]. Strain is lysine decarboxylase positive. Acid is produced from all Hugh and Leifson's O-F Medium, except in L-rhamnose, adonitol, inulin and salicin which were alkaline.

N. J. Palleroni and B. Holmes in their studies of *Pseudomonas cepacia* found that some strains hydrolyze gelatin and some give a positive lecithinase reaction [N. J. Palleroni and B. Holmes, October 1981. *Pseudomonas cepacia* Sp. nov., nom. rev., *International Journal of Systematic Bacteriology*, 31:479–481].

Palleroni, et al tested 19 strains and found that 16 strains hydrolyzed gelatin, and one gave a negative egg yolk reaction [R. Y. Stanier, N. J. Palleroni and M. Doudoroff, 1966. The Aerobic Pseudomonads: A Taxonomic Study, *J. Gen. Microbiol.*, 43:247–253] (see Table II).

Nutritional Properties:

No organic growth factors are required. Nutritionally, IFF-8296C is very versatile. Most of the organic compounds can be used as sole carbon and energy sources for growth. These compounds include a large variety of carbohydrates, mono- and dicarboxylic acids, mono- and polyalcohols, aromatic compounds, amino acids an amines. Lactose, maltose, L-rhamnose, adonitol, erythritol, geraniol, acetamide, testosterone, citraconate, L-(+)-tartrate, glycine, DL-norleucine, M-hydroxybenzoate, D-tryptophan, butylamine, mesaconate and methanol were not utilized by IFF-8296C for growth.

Palleroni, et al in their studies of 19 strains of *Pseudomonas cepacia* found 5 strains which lacked a series of nutritional characters otherwise practically constant for the group. One strain in their studies appeared to be the most defective in the whole collection: it was unable to grow in practical, universal substrates used by the group [R. Y. Stanier, N. J. Palleroni and M. Doudoroff, 1966. "The Aerobic Pseudomonads: A Taxonomic Study," *J. Gen. Microbiol.*, 43:247–253] (see Table II).

Antibiotic Susceptibilities:

The antibiotic susceptibilities of IFF-8296C as determined by standardized, single-disk diffusion tests was determined using 28 different antibiotics. IFF-8296C was resistant to 15 antibiotics tested, susceptible to 10 antibiotics and intermediate to 3 antibiotics. Antibiotic susceptibilities of *Pseudomonas cepacia* is from the studies of H. A. Sinsabaugh and G. W. Howard, Jr. [Henry A. Sinsabaugh and G. W. Howard, Jr., *International Journal of Systematic Bacteriology*, April 1975, pages 187–201]. Fifteen (15) strains of *Pseudomonas cepacia* were tested for antibiotic susceptibility (see Table III).

TABLE I*

MINIMAL CHARACTERS FOR IDENTIFICATION OF PSEUDOMONAD CEPACIA STRAINS

| Characters | Sign ± | % Positive | IFF-8296C |
|---|---|---|---|
| Polar tuft of 3 or more flagella per pole | + | 99 | + |
| Motility | + | 99 | + |
| O-F glucose medium, open, acid | + | 100 | + |
| O-F lactose medium, acid | + | 98 | + |
| O-F maltose medium, acid | + | 97 | + |
| O-F mannitol medium, acid | + | 100 | + |
| Nitrate to gas | − | 0 | − |
| L-lysine decarboxylase | + | 90 | + |
| L-arginine dihydrolase | − | 0 | − |

*G.L. Gilardi, 1985, Pseudomonas, page 361. In E.H. Lennette, A. Balows, W.J. Hausler, Jr. and H.J. Shadomy (editor), Manual of Clinical Microbiology, 4th edition, American Society for Microbiology, Washington, D.C.

TABLE II

GENERAL CHARACTERISTICS OF PSEUDOMONAS CEPACIA

| Characteristics | P. cepacia* | Type Strain** | IFF-8296C |
|---|---|---|---|
| Numer of flagella | >1 | >1 | >1 |
| Organic growth factor requirement | − | − | − |
| Oxidase reaction | + | + | + |
| Poly-β-hydroxybutyrate accumulation | + | + | + |
| Gelatin hydrolysis | d | + | − |
| Starch hydrolysis | − | − | − |
| Lecithinase (egg yolk) | d | + | + |
| Lipase (TWEEN ® 80 hydrolysis) | + | + | + |
| Denitrification | − | − | − |
| Reduction of nitrate to nitrite | + | − | + |
| Lysine decarboxylase | + | + | + |
| Growth at 4° C. | − | − | − |
| Growth at 42° C. | + | + | + |
| Carbon Sources Used for Growth: | | | |
| D-xylose | d | + | + |

TABLE II-continued

GENERAL CHARACTERISTICS OF PSEUDOMONAS CEPACIA

| Characteristics | *P. cepacia*\* | Type Strain\*\* | IFF-8296C |
|---|---|---|---|
| D-ribose | + | + | + |
| L-rhamnose | d | − | − |
| Mesaconate | − | − | − |
| Erythritol | − | − | − |
| Malonate | + | + | + |
| Adipate | + | + | + |
| Benzoate | + | + | + |
| D-alanine | + | + | + |
| L-valine | v | + | + |

KEY:
\* = Bergey's Manual of Systematic Bacteriology, Vol. 1, N.R. Krieg, ed., Williams & Wilkins, 1984.
\*\* = Type strain, ATCC 25416.
d = 11–89% strains are positive.
v = Results varies, i.e., variable results.

TABLE III

ANTIBIOTIC SUSCEPTIBILITIES OF IFF-8296C

|  |  | \*P. cepacia | | | IFF-8296C | | |
|---|---|---|---|---|---|---|---|
| Antibiotic | Potency | R | S | I | R | S | I |
| Amikacin | 30 | — | — | — |  | S |  |
| Ampicillin | 10 | 93% | 7% | 0% | R |  |  |
| Carbenicillin | 100 | 73% | 27% | 0% |  | S |  |
| Cefamandole | 30 | — | — | — | R |  |  |
| Cefotaxime | 30 | — | — | — |  | S |  |
| Cefoxitin | 30 | — | — | — | R |  |  |
| Cephalothin | 30 | 100% | 0% | 0% | R |  |  |
| Chloramphenicol | 30 | 7% | 73% | 20% |  | S |  |
| Clindamycin | 2 | — | — | — | R |  |  |
| Colistin | 10 | 93% | 7% | 0% | R |  |  |
| Erythromycin | 15 | 100% | 0% | 0% | R |  |  |
| Furadantin | 100 | — | — | — | R |  |  |
| Gentamycin | 10 | — | — | — |  |  | I |
| Kanamycin | 30 | — | — | — |  | S |  |
| Methicillin | 5 | 100% | 0% | 0% | R |  |  |
| Nafcillin | 1 | — | — | — | R |  |  |
| Nalidixic acid | 30 | 27% | 60% | 13% |  |  | I |
| Neomycin | 30 | 60% | 13% | 27% |  | S |  |
| Novobiocin | 30 | — | — | — |  | S |  |
| Oxicillin | 1 | — | — | — | R |  |  |
| Penicillin | 10 units | 100% | 0% | 0% | R |  |  |
| Polymixin B | 300 | — | — | — | R |  |  |
| Streptomycin | 10 | — | — | — | R |  |  |
| Tetracycline | 30 | 93% | 0% | 7% |  |  | I |
| Trimethoprim/Sulfamethoxazole | 1.25/23.75 | — | — | — |  | S |  |
| Tobramycin | 10 | — | — | — |  | S |  |
| Sulfisoxazole | .25 | — | — | — |  | S |  |
| Vancomycin | 30 | — | — | — | R |  |  |

Abbreviations:
R = resistant
S = susceptible
I = intermediate
Potency is the disk concentration in microorganisms except for penicillin which is expressed in international units.
— = not tested by investigator
\* = *Pseudomonas cepacia*: 15 strains tested by Henry A. Sinsabaugh and G.W. Howard, Jr. [Henry A. Sinsabaugh and G.W. Howard, Jr., International Journal of Systematic Bacteriology, April 1975, pages 187–201].

PHYSIOLOGY AND BIOCHEMISTRY:

| | | | |
|---|---|---|---|
| Gram positive | − | TWEEN ® 80 hydrolysis | + |
| Gram negative | + | Indole | − |
| Gram variable | − | Simmons citrate growth | + |

TABLE III-continued

| | | | |
|---|---|---|---|
| Motile | + | Urease | + |
| *Flagella peritrichous* | − | Nitrate to nitrite | + |
| *Flagella lophotrichous* | + | Nitrite reduction | − |
| *Flagella monotrichous* | − | Nitrite to nitrogen gas | − |
| *Flagella lateral* | − | Hydrogen sulfide (TSI)\* | − |
| 4 C. growth | − | Lysine decarboxylase | + |
| 26 C. growth | + | Arginine (Mollers) | − |
| 30 C. growth | + | Ornithine decarboxylase | − |
| 37 C. growth | + | Phenylalanine deamination | + |
| 42 C. growth | + | Lecithinase | + |
| Fluorescein produced | − | Phosphatase | + |
| Pyocyanine produced | − | Catalase | + |
| Diffusible orange | − | Oxidase | + |
| Diffusible yellow | − | Gluconate oxidation | − |
| Diffusible purple | − | Growth on malonate as SCS | + |
| Non-diffusible green | − | Tyrosine degradation | + |
| Other non-diffusible pigments | − | di-hydroxybutyrate growth | + |
| Melanin pigment produced | − | PHB accumulation | + |
| pH 6.0 growth | + | Growth on 0.05% cetrimide | + |
| 3% NaCl growth | + | Growth on acetate as SCS | + |
| 6.5% NaCl growth | − | Testosterone degradation | − |
| MacConkey agar growth | + | 1% NaCl growth | + |
| Skim milk agar growth | + | Mucoid growth on glucose agar | − |
| Aesculin hydrolysis | − | 0.1% TTC growth | + |
| Casein hydrolysis | + | 0.2% TTC growth | + |
| Starch hydrolysis | − | Litmus milk acid | + |
| Gelatinase | − | Litmus milk peptonized | + |
| TWEEN ® 20 hydrolysis | + | | |

\*Lead acetate strip: negative
Gelatin tube: negative

REACTIONS IN HUGH & LEIFSON'S MEDIUM:

| Acid from: | | Acid from: | |
|---|---|---|---|
| L-arabinose | + | D-mannose | + |
| cellobiose | + | L-rhamnose | K |
| ethanol | + | D-ribose | + |
| D-fructose | + | sucrose | + |
| D-glucose AO$_2$ | + | trehalose | + |
| D-glucose AnO$_2$ | − | D-xylose | + |
| Alkaline pH in D-glucose | − | adonitol | K |
| Acid from: | | dulcitol | + |
| glycerol | + | D-galactose | + |
| i-inositol | + | inulin | K |
| lactose | + | salicin | K |
| maltose | + | D-sorbitol | + |
| D-mannitol | + | | |
| | | Control | K |

K = alkaline

SOLE CARBON SOURCE IN STANIER'S MINERAL BASE:

| | | | |
|---|---|---|---|
| L-arabinose as SCS | + | 2-ketogluconate as SCS | + |
| cellobiose as SCS | + | DL-lactate as SCS | + |
| D-fructose as SCS | + | L-malate as SCS | + |
| D-glucose as SCS | + | pelargonate as SCS | + |
| lactose as SCS | − | propionate as SCS | + |
| maltose as SCS | − | quinate as SCS | + |
| D-mannitol as SCS | + | succinate as SCS | + |
| L-rhamnose as SCS | − | L-+-tartrate as SCS | − |
| D-ribose as SCS | + | valerate as SCS | + |
| D-sorbitol as SCS | + | B-alanine as SCS | + |
| sucrose as SCS | + | D-A-alanine as SCS | + |
| trehalose as SCS | + | betaine as SCS | + |
| D-xylose as SCS | + | glycine as SCS | − |
| adonitol as SCS | − | L-histidine as SCS | + |
| erythritol as SCS | − | DL-norleucine as SCS | − |
| glycerol as SCS | + | L-proline as SCS | + |
| ethanol as SCS | + | D-tryptophan as SCS | − |
| geraniol as SCS | − | L-valine as SCS | + |
| i-inositol as SCS | + | DL-arginine as SCS | + |
| sebacic acid as SCS | + | benzylamine as SCS | + |
| acetamide as SCS | − | butylamine as SCS | − |
| adipate as SCS | + | putrescine as SCS | + |
| benzoate as SCS | + | mesaconate as SCS | − |
| butyrate as SCS | + | DL-glycerate as SCS | + |

TABLE III-continued

| | | | |
|---|---|---|---|
| citraconate as SCS | − | L-tryptophan as SCS | + |
| D-gluconate as SCS | + | Methanol as SCS | − |
| M-hydroxybenzoate as SCS | − | | |

SCS = Sole Carbon Source

REFERENCES:
1. *Bergey's Manual of Systematic Bacteriology*, Vol. 1, N. R. Krieg (ed.), Williams & Wilkins, 1984.
2. Gilardi, G. L., 1985, *Pseudomonas*, pages 361–362, In E. H. Lennette, A. Balows, W. J. Hausler, Jr., and H. J. Shadomy (ed.), *Manual of Clinical Microbiology*, 4th Edition, American Society for Microbiology, Washington, D.C.
3. Palleroni, N. J., B. Holmes, October 1981, *Pseudomonas cepacia*, sp. nov., nom. rev. *International Journal of Systematic Bacteriology*, 31, pages 479–481.
4. Sinsabaugh, H. A. and G. W. Howard, Jr., April 1975, "Emendation of the Description of *Pseudomonas cepacia* Buckholder" (synonyms: *Pseudomonas multivorans* Stanier, et al, *Pseudomonas kingae* Jonsson; EO-I Group), *International Journal of Systematic Bacteriology*, pages 187–201.
5. Stanier, R. Y., N. J. Palleroni and M. Doudoroff, 1966, "The Aerobic Pseudomonads: A Taxonomic Study," *J. Gen. Microbiol.*, 43, pages 247–253.

The mixture of alcohols of this invention defined according to the structures:

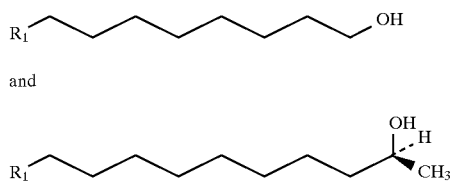

wherein $R_1$ is methyl or n-propyl can be added to flavor and/or perfume compositions in a pure form, or they can be added to mixtures of materials in flavor and/or fragrance imparting compositions to provide a desired organoleptic or fragrance character to the finished flavor or perfume material (as the case may be). The flavor, perfume and fragrance compositions obtained according to this invention are suitable in a wide variety of foodstuffs and perfumed articles and can also be used to improve, enhance, modify, alter or reinforce natural flavor and fragrance materials. It will thus be appreciated that the mixture of alcohols of this invention are useful as olfactory agents and fragrances or organoleptic agents and flavors.

The term "perfume composition" is used herein to mean a mixture of compounds including, for example, natural oils, synthetic oils, alcohols other than the mixture of alcohols of our invention, aldehydes, ketones, esters, lactones and frequently, hydrocarbons which are admixed so that the combined odors of the individual components produce a pleasant or desired fragrance. Such perfume compositions usually contain: (a) the main note or the "bouquet" or foundation stone of the composition; (b) modifiers which round off and accompany the main note; (c) fixatives which include odorous substances which lend a particular note to the perfume throughout all stages of evaporation, and substances which retard evaporation; and (d) topnotes which are usually low boiling, fresh smelling materials.

Such perfume compositions or the novel mixtures of this invention can be used in conjunction with carriers, vehicles, solvents, dispersants, emulsifiers, surface-active agents, aerosol propellants and the like. In perfume compositions, the individual components contribute their particular olfactory characteristics, but the overall effect of the perfume composition will at least be the sum of the effect of each ingredient. Thus, the mixture of alcohols of this invention can be used to alter the aroma characteristics of a perfume composition, for example, by highlighting or moderating the olfactory reaction contributed by another ingredient of the composition.

The amount of the mixture of the alcohols of this invention which will be effective in perfume compositions depends on many factors including the other ingredients, their amounts and the effects which are desired. It has been found that perfume compositions containing as little as 1.0% by weight of the mixture of alcohols of this invention or even less can be used to intensify or augment and enhance various types of fragrance compounds, the odors of which may be desired to be imparted to colognes, perfumes, bath oils and other cosmetic products. The amount employed will depend on consideration of cost, nature of the end product, the effect desired in the finished product and the particular fragrance sought. Higher concentrations (e.g., 4% by weight) of the mixture of alcohols of this invention will intensify the floral and citrusy notes of the compositions.

The mixture of alcohols disclosed herein can also be used in a composition as an olfactory component of the fragrance which, in turn, can be used in perfumes, colognes, bath preparations (such as bath oils and bath salts) and the like. When the mixture of alcohols are used in finished perfumed articles such as the foregoing, they can be used in amounts of 0.04% or lower.

When used to impart, alter, modify or enhance flavors in foodstuffs, the novel mixtures of alcohols of our invention may be employed either singly or in admixture with one another. In this manner, the processor is afforded means whereby to exploit the beneficial nature of each of a plurality of materials in a specific instance.

In many instances, the optimum balance of flavor is obtained by utilizing the mixture of alcohols of our invention with other co-ingredients. The nature of the co-ingredients included with the mixture of the alcohols of our invention in formulating the product composition will, of course, depend primarily upon the ultimate use contemplated, i.e., as a foodstuff per se or alternatively as a flavoring composition adapted to be added to a foodstuff at some subsequent point in time. In any event, such compounds serve to alter the organoleptic characteristics of the ultimate foodstuffs treated therewith.

Substances suitable for use herein as co-ingredients or flavoring adjuvants are well known in the art for such use being extensively described in the relevant literature. Apart from the requirement that any such material be "ingestibly" acceptable, and thus non-toxic or otherwise non-deleterious, nothing particularly critical resides in the selection thereof. Accordingly, such materials which may in general be characterized as flavoring adjuvants or vehicles comprise broadly, stabilizers, thickeners, surface active agents, conditioners, flavorants and flavor intensifiers.

Stabilizer compounds include preservatives, e.g., sodium chloride, antioxidants, e.g., calcium and sodium ascorbate, ascorbic acid, butylated hydroxyanisole (mixture of 2 and 3 tertiary butyl-4-hydroxyanisoles), butylated hydroxy toluene (2,6-di-tertiary-butyl-4-methyl phenol), propyl gallate and the like, and sequestrants, e.g., citric acid.

Thickener compounds include carriers, binders, protective colloids, suspending agents, emulsifiers and the like, e.g., agar-agar; carrageenan; cellulose derivatives such as carboxymethyl cellulose and methyl cellulose; natural and synthetic gums such as gum arabic, gum tragacanth; gelatin, proteinaceous materials, lipids; carbohydrates; starches; pectins and emulsifiers, e.g., mono- and diglycerides of fatty acids, skim milk powder, hexoses, pentoses, disaccharides, e.g., sucrose, corn syrup solids and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like; buffers and neutralizing agents, e.g., sodium acetate, ammonium bicarbonate, ammonium phosphate, citric acid, lactic acid, vinegar and the like; colorants, e.g., carminic acid, cochineal, tumeric and curcumin and the like; firming agents such as aluminum sodium sulfate, calcium chloride and calcium gluconate; texturizers; anti-caking agents, e.g., aluminum calcium phosphate; enzymes; yeast foods, e.g., calcium lactate and calcium sulfate; nutrient supplements, e.g., iron salts such as ferric phosphate, ferric pyrophosphate, ferrous gluconate and the like, riboflavin, vitamins, zinc sources such as zinc chloride, zinc sulfate and the like.

Flavorants and flavor intensifiers include organic acids, e.g., fatty saturated, unsaturated and amino acids; alcohols other than the mixtures of alcohols of our invention, e.g., primary and secondary alcohols; esters, carbonyl compounds including aldehydes and ketones, lactones; cyclic organic materials such as benzene derivatives; alicyclics, heterocyclics such as furans, particularly 3-acetylfuran, alkyl pyridines, alkyl and polyalkyl pyrazines and the like; sulfur-containing materials including thiazoles, thiols, sulfides, disulfides and the like; so-called flavor potentiators such as monosodium glutamate, tetramethyl pyrazine, guanylates, inosinates, natural and synthetic flavorants such as vanillin, ethyl-vanillin, diacetyl, phenethyl-2-furoate, maltol, natural gums and the like; spices, herbs, essential oils and extractives including "bitterness principles" such as theobromin, caffeine, naringin and other suitable materials creating a bitter effect.

The specific flavoring adjuvants selected for use may be either solid or liquid, depending upon the desired physical form of the ultimate product, i.e., foodstuffs, whether simulated or natural and should, in any event, be capable of providing an environment in which the mixture of alcohols of our invention can be dispersed or admixed to provide a homogeneous medium. In addition, selection of one or more flavoring adjuvants as well as the quantities thereof will depend upon the precise organoleptic character desired in the finished product; thus, in the case of flavoring compositions, ingredient selection will vary in accordance with the foodstuffs to which the flavor and aroma are to be imparted. In contra-distinction in the preparation of solid products, e.g., simulated foodstuffs, ingredients capable of providing normally solid compositions should be selected such as various cellulose derivatives.

As will be appreciated by those skilled in the art, the amount of the mixture of alcohols of our invention employed in a particular instance can vary over a relatively wide range whereby to achieve desired organoleptic effects having reference to the nature of the product. All parts and percentages given herein are by weight unless otherwise specified. Thus, correspondingly greater amounts would be necessary in those instances wherein the ultimate food composition to be flavored is relatively bland to the taste, whereas relatively minor quantities may suffice for purposes of enhancing a composition merely deficient in natural flavor or aroma. Thus, the primary requirement is that the amount selected be effective, i.e., sufficient to alter the organoleptic character of the parent composition whether the foodstuff per se or flavorant composition.

Thus, the use of insufficient quantities of the mixture of alcohols of our invention will, of course, substantially vitiate any possibility of obtaining the desired results while excess quantities prove needlessly costly and, in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects. Thus, and with respect to ultimate food compositions, it is found that quantities of the mixture of alcohols of our invention ranging from a small but effective amount, e.g., 1.0 part per million up to about 200 parts per million by weight based on total composition are suitable. Concentrations in excess of the maximum quantities stated are not normally recommended since they fail to provide commensurate enhancement of organoleptic properties. In those instances wherein the mixture of alcohols of our invention is added to the foodstuff as an integral component of a flavoring composition, it is, of course, essential that the total quantity of flavoring composition employed be sufficient to yield an effective alcohol mixture concentration in the foodstuff product.

The following Examples I-XVIII serve to illustrate embodiments of the invention for production and purification of the mixture of alcohols and alcohols per se of our invention as it is now preferred to practice it. Examples following Example XVIII, Example XIX, et seq., indicate uses of the mixture of alcohols of our invention for their organoleptic properties.

It will be understood that these examples are illustrative and the invention is to be considered restricted thereto only as indicated in the appended claims.

EXAMPLE I

Natural Nonyl Alcohol Production Using *Pseudomonas Cepacia* ATCC 55792

Reaction:

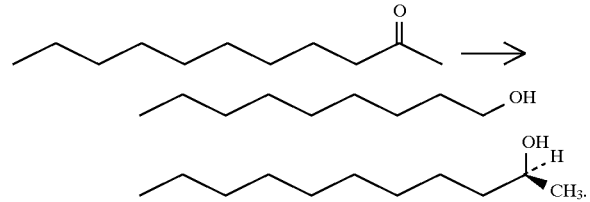

Inoculum Preparation:
  (i) Medium
  0.1% $NH_4NO_3$;
  0.1% $KH_2PO_4$;
  0.05% $MgSO_4.7H_2O$;
  0.2% TASTONE® 900 (yeast extract, Trademark of Red Star BioProduct Division of Universal Food Corporation of 433 East Michigan Street, Milwaukee, Wis. 53201); and 0.05% TWEEN® 80.

The pH of the resulting mixture is adjusted to 6.5 prior to sterilization. After sterilization, add 1% hexadecane to the flask.

(ii) Inoculum

2 Ml of medium is used to wash a slant of *Pseudomonas cepacia* ATCC 55792. Then the wash is used to inoculate 100 ml of media.

(iii) Conditions

Temperature: 28° C.;

Agitation: 150 RPM; and

Incubation time: 24 hours.

Production:

10 Liters of the following medium was prepared in a 14 liter fermenter and sterilized at 121° C. for 20 minutes:

| Production Medium | |
|---|---|
| Ingredient | Grams per Liter |
| NH$_4$NO$_3$ | 1.0 |
| KH$_2$PO$_4$ | 1.0 |
| MgSO$_4$.7H$_2$O | 0.5 |
| TASTONE ® 900 | 2.0 |
| TWEEN ® 80 | 0.5 |

After sterilization, the fermenter was inoculated with 100 ml 24 hour-grown inoculum produced, supra. 200 Grams of natural 2-undecanone was then added to the resulting mixture in the fermenter with stirring.

Process Perameters:

Temperature: 30° C.;

Aeration: 0.4 v/v/m; and

Agitation: 800 RPM.

The pH of the reaction mass is automatically controlled at 6.5 using 20% aqueous ammonia. After 6 days while maintaining the fermentation at 30° C and the pH at 6.5, 75 grams of 87% pure nonyl alcohol was recovered by steam distillation directly the fermenter. The remaining product is dextrorotatory 2-undecanol having the structure:

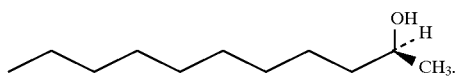

The resulting product is fractionally distilled yielding the following fractions:

| Fraction Number | Vapor Temperature (°C.) | Liquid Temperature (°C.) | Vacuum mm/Hg Pressure | Reflux Ratio |
|---|---|---|---|---|
| 1 | 20/23 | 23/110 | 200 | 100% |
| 2 | 115 | 135 | 350 | 100% |
| 3 | 128 | 138 | 400 | 9:1 |
| 4 | 128 | 138 | 400 | 9:1 |
| 5 | 130 | 135 | 400 | 9:1 |
| 6 | 131 | 135 | 400 | 9:1 |
| 7 | 131 | 138 | 400 | 9:1 |
| 8 | 132 | 138 | 400 | 9:1 |
| 9 | 132 | 138 | 400 | 9:1 |
| 10 | 132 | 138 | 400 | 9:1 |
| 11 | 132 | 139 | 400 | 9:1 |
| 12 | 132 | 138 | 400 | 9:1 |
| 13 | 132 | 138 | 400 | 9:1 |
| 14 | 132 | 138 | 400 | 9:1 |
| 15 | 132 | 138 | 400 | 9:1 |
| 16 | 132 | 138 | 400 | 9:1 |
| 17 | 133 | 138 | 400 | 9:1 |
| 18 | 132 | 138 | 400 | 9:1 |
| 19 | 132 | 138 | 400 | 9:1 |
| 20 | 132 | 138 | 400 | 9:1 |
| 21 | 132 | 138 | 400 | 9:1 |
| 22 | 132 | 138 | 400 | 9:1 |
| 23 | 132 | 138 | 400 | 9:1 |
| 24 | 133 | 140 | 400 | 9:1 |
| 25 | 133 | 140 | 400 | 9:1 |
| 26 | 133 | 142 | 400 | 9:1 |
| 27 | 133 | 145 | 400 | 9:1 |
| 28 | 133 | 145 | 400 | 9:1 |
| 29 | 133 | 145 | 400 | 9:1 |
| 30 | 132 | 145 | 400 | 9:1 |
| 31 | 132 | 148 | 400 | 9:1 |
| 32 | 132 | 150 | 400 | 9:1 |
| 33 | 132 | 152 | 400 | 9:1 |
| 34 | 148 | 155 | 400 | 9:1 |
| 35 | 148 | 155 | 400 | 9:1 |
| 36 | 150 | 158 | 400 | 9:1 |
| 37 | 148 | 158 | 400 | 9:1 |
| 38 | 146 | 166 | 400 | 9:1 |
| 39 | 145 | 165 | 400 | 9:1 |
| 40 | 133 | 220 | 400 | 9:1 |

Fractions 9–33 are bulked. Bulked distillation fractions 9–33 contain the compound having the structure:

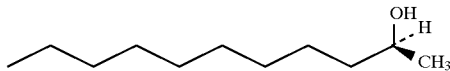

and the compound having the structure:

as confirmed by NMR, IR and mass spectral analyses. The resulting product is used for its organoleptic utilities as set forth in Examples XIX, et seq., infra.

EXAMPLE I-M

Formation of Mutants of Pseudomonas Cepacia ATCC 55792

(1) Medium 0.2% TASTONE® 900;

0.1% NH$_4$NO$_3$;

0.1% KH$_2$PO$_4$;

0.05% MgSO$_4$.7H$_2$O; and 0.05% TWEEN® 80.

The pH of the resulting medium is adjusted to 6.5 prior to sterilization using sodium hydroxide. After sterilization, 1% sterile CERELOSE® 2001 is added to the mixture.

(2) A 500 ml flask containing 100 ml of the above medium (produced according to step 1) was inoculated with 2 ml of a frozen culture of *Pseudomonas cepacia* ATCC 55792. This flask is then incubated at 28° C. with shaking at 150 RPM for 18–24 hours.

(3) A 500 ml flask containing 100 ml of the above medium (produced according to step (1)) was inoculated with 10 mil of the culture produced according to step (2) above and incubated for 4 hours.

(4) 2 Ml of the 4-hour culture produced according to step (3) were centrifuged and the resulting cell pellet was washed twice with 2 ml of sterile 0.1M sodium phosphate buffer (pH=7.0).

(5) The resulting pellet produced according to step (4) was suspended in 1 ml of buffer and 50 μl ethyl methanesulfonate (EMS produced by Eastman Kodak Corporation of Rochester, N.Y.) was added. The suspension was then placed on a rotating platform and incubated for 1 hour at 28° C.

(6) Mutagenesis was terminated by the addition of 8 ml of 5% sodium thiosulfate to 0.2 ml of the EMS-treated cells. Serial dilutions of this culture were plated on the following two media and incubated at 28° C. for 48 hours:

(a) the medium of step (1) with 2% agar added; and
(b) the medium of step (1) with 2% agar added, except that the dextrose is replaced with 95% foodgrade ethanol.

(7) Colonies which grew on the sugar-containing medium, but did not grow on the ethanol-containing medium (ethanol negative) were isolated for reaction.

Three different isolates thus produced were used in Examples IV, VI and IX, infra, respectively.

EXAMPLE II

Reaction:

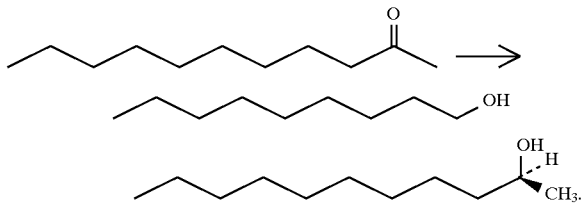

The above reaction is carried out in the same manner as in Example I, except that the dextrose was replaced with 1% undecanone in the inoculum flask. After 6 days, 67.2 grams of 82.6% of pure nonyl alcohol was recovered through steam distillation with the remainder being the optical isomer having the structure:

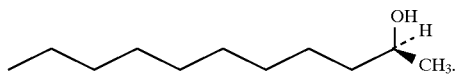

EXAMPLE III

Reaction:

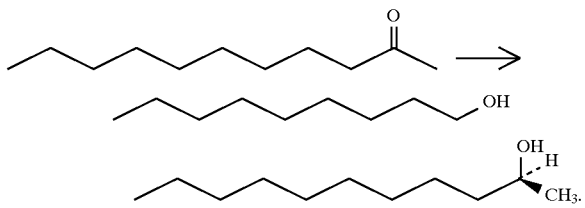

The foregoing reaction was carried out in the same manner as in Example II, except that, initially, the pH was maintained at 7.5 and the aeration rate was 0.1 v/v/m. After 88 hours, the pH was lowered to 6.5 and the aeration rate was increased 0.4 v/v/m. After 10 days, 66 grams of 87% pure nonyl alcohol was recovered through steam distillation with the remainder of the product being the optical isomer having the structure:

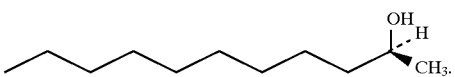

EXAMPLE IV

Reaction:

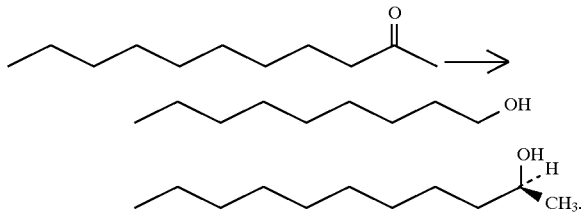

The foregoing reaction was carried out in the same manner as in Example I, except that a mutant of *Pseudomonas cepacia* ATCC 55792 produced according to Example I-M was used. After 10 days, 83 grams of 91.9% pure nonyl alcohol was recovered through steam distillation with the remainder being the optical isomer having the structure:

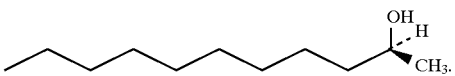

EXAMPLE V

Reaction:

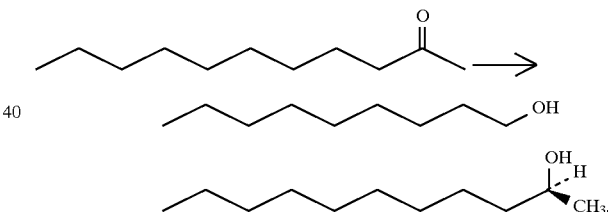

The foregoing reaction was carried out in the same manner as in Example I, except that 0.25% sterile glucose solution was added to the fermenter at the time of inoculation. The undecanone was then added 18 hours later. After 7 days, 100 grams of 85.5% pure nonyl alcohol was recovered through steam distillation with the remainder of the product being the optical isomer having the structure:

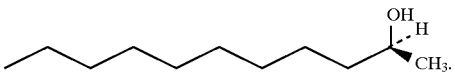

EXAMPLE VI

Reaction:

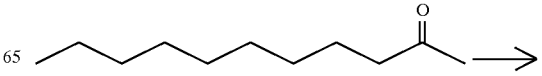

Reaction:

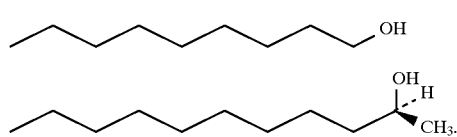

The foregoing reaction was carried out in the same manner as in Example V, except that the mutant produced according to Example I-M, supra, was used. After 13 days, 96.5 grams of 85.0% pure nonyl alcohol was recovered through steam distillation with the remainder being the stereo isomer having the structure:

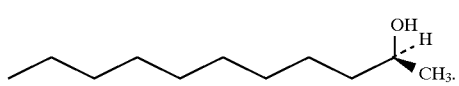

EXAMPLE VII

Reaction:

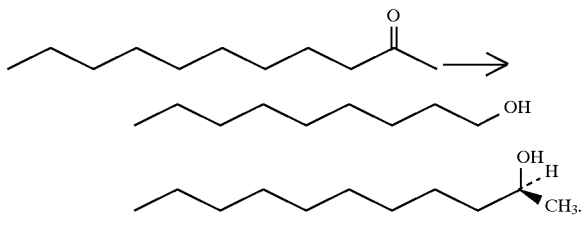

The foregoing reaction was carried out in the same manner as in Example V, except that 0.5% sterile glucose solution was used. After 5 days, 80.0 grams of 89.7% pure nonyl alcohol was recovered through steam distillation with the remainder being the stereo isomer having the structure:

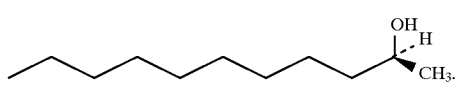

EXAMPLE VIII

Reaction:

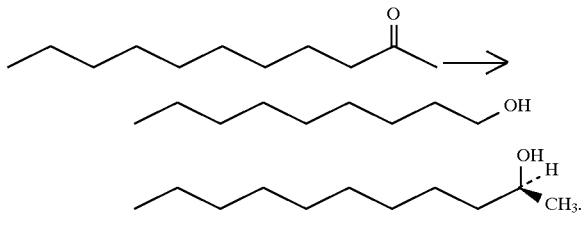

The foregoing reaction was carried out in the same manner as in Example V, except that 0.375% sterile glucose solution was used and the inoculum was grown on 1% sugar. After 6 days, 93.8 grams of 92.9% pure nonyl alcohol was recovered through steam distillation with the remainder of the product being the stereo isomer having the structure:

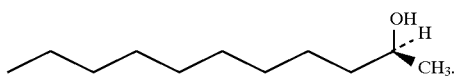

EXAMPLE IX

Reaction:

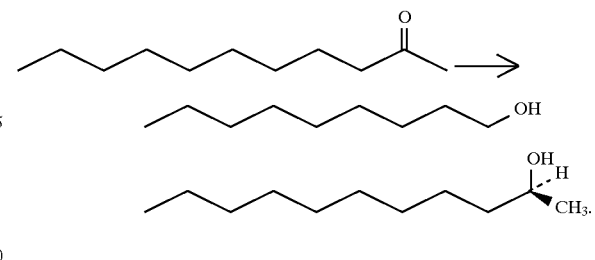

The foregoing reaction was carried out in the same manner as in Example VIII, except that a mutant prepared according Example I-M was used. After 7 days, 87.8 grams of 77.3% pure nonyl alcohol was recovered through steam distillation with the remainder of the product being the stereo isomer having the structure:

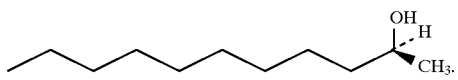

A distillation cut containing 72% 1-nonanol and 18% 2-undecanol has an optical rotation of +0.73°.

EXAMPLE X

Reaction:

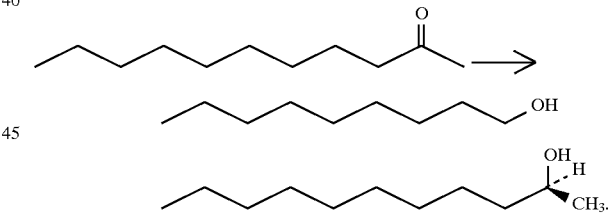

The foregoing reaction was carried out in the same manner as in Example VIII, except that when the undecanone was added to the fermenter, the aeration rate was reduced to 0.1 v/v/m and back pressure was set at 10 psig. After 9 days, 97.4 grams of 46.9% pure nonyl alcohol was recovered through steam distillation with the remainder of the product being the stereo isomer having the structure:

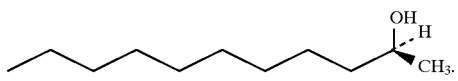

A distillation cut containing 50% 1-nonanol and 37% 2-undecanol had an optical rotation of +0.24°. A distillation cut containing 96% 2-undecanol and 3.6% 2-undecanone had an optical rotation of +3.44°.

EXAMPLE XI

Reaction:

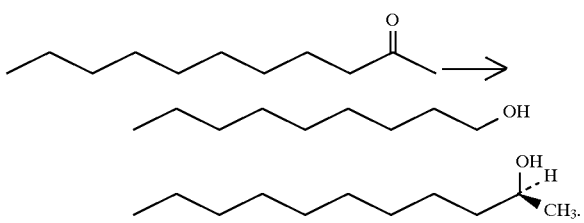

The foregoing reaction was carried out in the same manner as in Example VIII, except that when the undecanone was added to the fermenter, the aeration rate was reduced to 0.1 v/v/m and the temperature was lowered to 25° C. After 7 days, 84.5 grams of 87.8% pure nonyl alcohol was recovered through steam distillation with the remainder of the product being the stereo isomer having the structure:

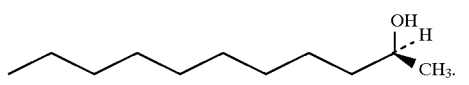

EXAMPLE XII

Reaction:

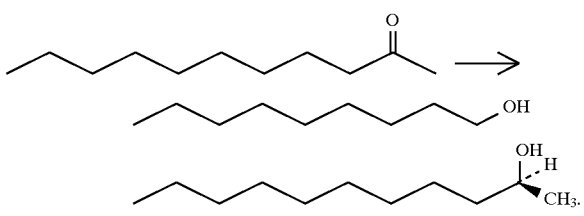

The foregoing reaction was carried out in the same manner as in Example XI, except that instead of adding all of the 2-undecanone at once, it was slowly pumped into the fermenter over a 24-hour period. After 7 days, 43.9 grams of 77.1% pure nonyl alcohol was recovered through steam distillation with the remainder of the product being the stereo isomer having the structure:

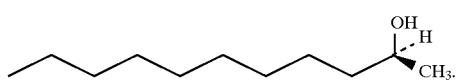

EXAMPLE XIII

Reaction:

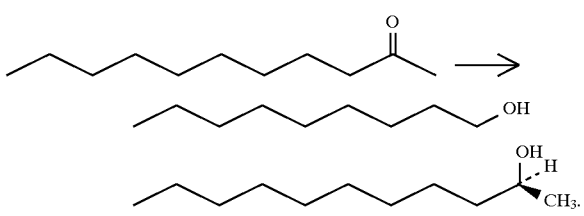

The foregoing reaction was carried out in the same manner as in Example VIII, except that after 24 hours, the cooling water to the condenser was turned off and a charcoal trap was connected to the fermenter exhaust line. After 5 days, 92.8 grams of 90% pure nonyl alcohol was recovered from the fermenter during steam distillation with the remainder of the product being the stereo isomer having the structure:

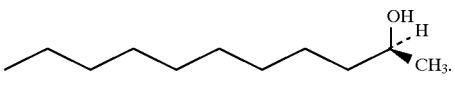

Nothing was recovered from the charcoal trap.

EXAMPLE XIV

Reaction:

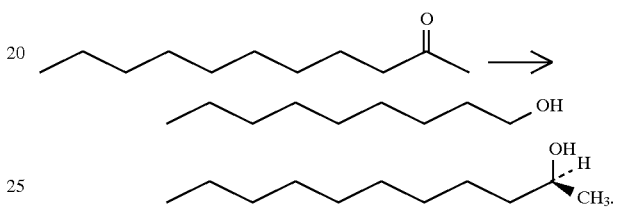

The foregoing reaction was carried out in the same manner as in Example XIII, except that 20% aqueous sodium hydroxide was used for maintaining the pH throughout the fermentation. After 6 days, 100.5 grams of 88.3% pure nonyl alcohol was recovered through steam distillation with the remainder of the product being the stereo isomer having the structure:

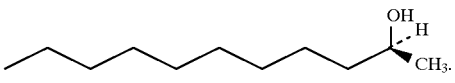

EXAMPLE XV

Reaction:

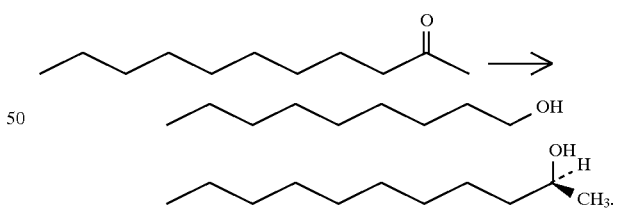

The foregoing reaction was carried out in the same manner as in Example XIV, except that 5 grams per liter of TASTONE® 900 was used in the fermenter. After 5 days, 23.6 grams of 72.4% pure nonyl alcohol was recovered through steam distillation with the remainder of the product being the stereo isomer having the structure:

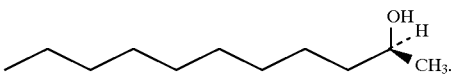

EXAMPLE XVI

Reaction:

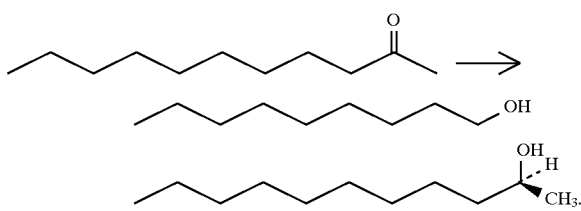

An 800 liter batch was carried out in the same manner as in Example V, except that 50% aqueous sodium hydroxide was used for maintaining the pH throughout the fermentation. After 8 days, a total of 6.95 kg of crude nonyl alcohol with a purity of 94.4% was recovered by steam distillation. The nonyl alcohol was further purified by fractional distillation as set forth in Example I yielding fractions boiling at a vapor temperature of 132–133° C. and a liquid temperature of 138–150° C. at a pressure of 400 mm/Hg. The remainder of the product is the optical isomer having the structure:

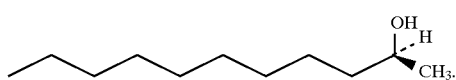

EXAMPLE XVII

Reaction:

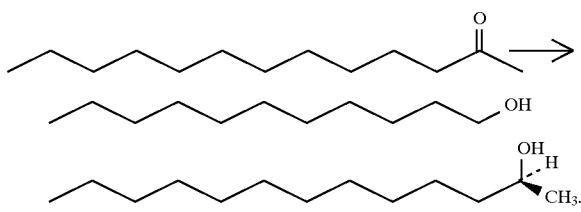

100 Ml of inoculum medium is placed in a 500 ml flask. The inoculum medium is sterilized in the flask at 121° C. for a 20-minute period. After sterilization, 1% tridecanone having the structure:

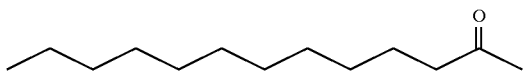

and 1% of 24 hour-sugar-grown inoculum were added to the reaction mass. The resulting culture is placed in an incubator-shaker operated at 150 RPM at 28° C. for a period of 72 hours. The contents of the flask were then extracted with ethyl acetate and the solvent was then removed under vacuum. A total of 0.42 grams of crude extract containing 85.4% undecanol having the structure:

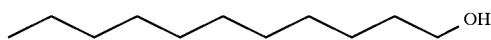

and 10.5% tridecanone having the structure:

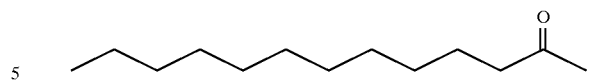

was obtained. The remainder of the mixture is the stereo isomer having the structure:

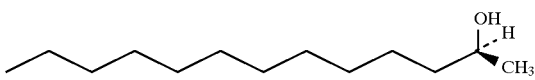

(as confirmed by NMR, IR and mass spectral analyses). A distillation cut containing 99% 2-undecanol at an optical rotation of +3.44°.

EXAMPLE XVIII

Purification of Natural Nonyl Alcohol

The crude, extracted, natural nonyl alcohol of Example XVI contained as the major impurity 2-undecanol having the structure:

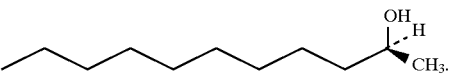

These two materials readily separate by distillation. However, the product also contained a small amount of unsaturated C-9 amine having the structure:

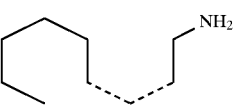

which is a mixture of compounds wherein in the mixture one of the dashed lines is a carbon carbon double bond and the other of the dashed lines is a carbon carbon single bond. This unsaturated C-9 amine boils very closely to the main component. It can degrade flavor quality if not removed. In addition, the presence of small amounts of residual methly nonyl ketone having the structure:

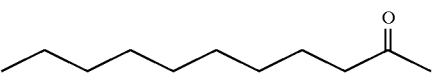

as well as related ketones can cause a problem during the purification. Even though these ketones are higher boiling than nonyl alcohol, they co-distill. Accordingly, using the reactions:

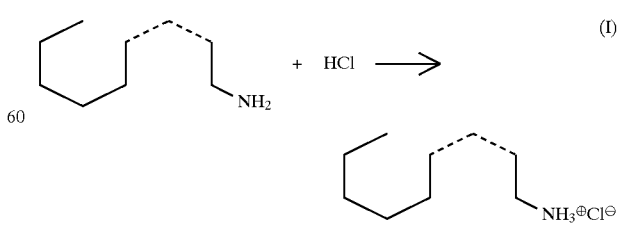

and

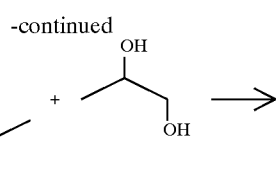

these impurities can be removed.

Thus, the amine impurity in the crude is easily removed by extraction with dilute acid such as hydrochloric acid. Other acids such as citric acid and acetic acid can also be used. The methyl nonyl ketone and isomers thereof, if over 1% in the crude (compared to the nonyl alcohol), must be chemically converted to the corresponding cyclic ketal via reaction with 1,2-propylene glycol as set forth in the above reaction. The corresponding dioxylane derivative is higher boiling than the 2-undecyl alcohol and can be readily separated by distillation. To accomplish this, the crude reaction mixture is reacted with 1,2-propylene glycol in the presence of paratoluene sulfonic acid in boiling cyclohexane. The ketal (dioxolane) made from ethylene glycol is not high boiling enough. While these ingredients are not "flavor natural" per se, they do not react in any way with nonyl alcohol. They react solely with with the ketonic side products.

Procedure

Materials:

Crude nonyl alcohol produced according to Example XVI, quantity . . . 1,740 grams;

Cyclohexane . . . 1,500 grams;

Paratoluene sulfonic acid . . . 5 grams;

1,2-Propylene glycol . . . 50 grams;

5% aqueous hydrochloric acid . . . 500 ml; and

5% aqueous sodium hydroxide solution . . . 1,000 ml.

Equipment:

5 Liter flask is equipped with an overhead stirrer, Bidwell trap, condenser, heating mantle, thermometer, sepatory funnel and 18"×1.5" Goodloe packed column.

Action:

(1) The crude-washed nonyl alcohol is extracted once with 500 ml of 5% aqueous hydrochloric acid to remove acid notes. The acid wash should precede the ketal formation step. Dilute acid can partially hydrolyze the ketal-releasing free methyl nonyl ketone;

(2) The organic layer is charged to the flask along with the cyclohexane, the propylene glycol and the paratoluene sulfonic acid. The solution is heated at reflux for 2 hours, separating out any water formed;

(3) The organic layer is cooled and washed with 5% aqueous sodium hydroxide. The resulting product has a GC-capillary survey as set forth in FIGS. 4A and 4B; and (4) The crude product, weighing 2,896 grams and having a total ion chromatogram as set forth in FIG. 3, is charged to the still. The solvent is removed at atmospheric pressure to a pot temperature of 120° C. The pressure is slowly reduced to 400 mm/Hg. The resulting product is distilled off at a reflux ratio of 9:1, boiling at 132° C. to a final pot temperature of 160° C.

35 Fractions were collected. Fractions 9–33 were bulked and flavor approved.

EXAMPLE XIX

The following composition is prepared:

| Ingredients | Parts by Weight |
| --- | --- |
| Bergamot oil | 120 |
| Methyl ionone | 60 |
| Jasmine extra | 80 |
| Petitgrain oil | 60 |
| Patchouli oil | 60 |
| Violet perfume base | 60 |
| Mixture of the compound having the structures: | 20 |

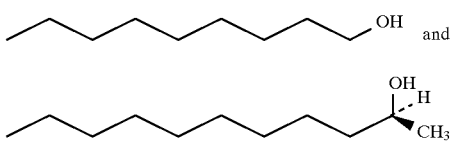

prepared according to Example I, bulked distillation fractions 9–33.

| | |
| --- | --- |
| Lemon oil | 80 |
| Rose geranium oil | 120 |
| Lavender oil, French | 120 |
| Sweet orange oil | 80 |
| Musk extract 3% in diethylphthlate | 50 |
| Civet extract, 3% in diethylphthlate | 50 |

The addition of the mixture of compounds having the structures:

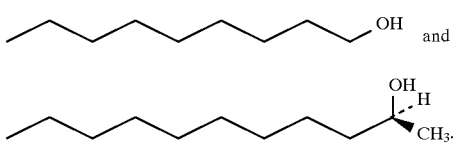

prepared according to Example I improve the overall citrus/floral quality of the instant formulation, lending a more neroli oil-like and coriander-like effect thereto. Thus, the fragrance can be described as:

"a citrus and floral aroma having neroli oil-like and coriander topnotes".

EXAMPLE XX

Cosmetic Powder Preparation

A cosmetic powder is prepared by mixing in a ball mill 100 grams of talcum powder with 0.25 grams of one of the substances set forth in Table IV below containing the mixture of compounds having the structures:

Each of the cosmetic powders has an excellent aroma as described in Table IV below.

TABLE IV

| Perfumery Substance | Aroma Nuance |
|---|---|
| The mixture of compounds having the structures:<br><br>CH$_3$(CH$_2$)$_6$CH$_2$—OH<br><br>and<br><br>CH$_3$(CH$_2$)$_6$CH(OH)—CH(H)—CH$_3$<br><br>prepared according to Example I. | A floral and citrusy aroma with neroli oil and coriander topnotes. |
| Perfume composition of Example XIX. | A citrus and floral aroma having neroli oil-like and coriander topnotes. |
| The mixture of compounds having the structures:<br><br>CH$_3$(CH$_2$)$_7$CH$_2$—OH<br><br>and<br><br>CH$_3$(CH$_2$)$_7$CH(OH)—CH(H)—CH$_3$<br><br>prepared according to Example XVII. | A sweet, citrusy and floral aroma with violet and cassis topnotes. |

EXAMPLE XXI

Pered Liquid Detergents

Concentrated liquid detergents (lysine salt of n-dodecylbenzene sulfonic acid as more specifically described in U.S. Pat. No. 3,948,818 issued Apr. 6, 1976, the specification for which is incorporated by reference herein) with aroma nuances as set forth in Table IV of Example XX are prepared containing 0.10%, 0.15%, 0.20%, 0.25%, 0.30% and 0.35% of the substance set forth in Table IV of Example XX. They are prepared by adding and homogeneously mixing the appropriate quantity of one of the substances set forth in Table IV of Example XX in the liquid detergent. The detergents all possess excellent aromas as set forth in Table IV of Example XX.

EXAMPLE XXII

Preparation of Cologne and Handkerchief Perfumes

The substances set forth in Table IV of Example XX, are incorporated separately into colognes at concentrations 2.0%, 2.5%, 3.0%, 3.5%, 4.0%, 4.5% and 5.0% in 75%, 80%, 85% and 90% aqueous food grade ethanol solutions; and into handkerchief perfumes at concentrations of 15%, 20%, 25% and 30% in 80%, 85%, 90% and 95% aqueous food grade ethanol solutions. Distinctive aromas as set forth in Table IV of Example XX are imparted to the colognes and to the handkerchief perfume compositions at all levels indicated.

EXAMPLE XXIII

Preparation of Soap Composition

100 Grams of soap chips (IVORY® produced by the Procter & Gamble Company of Cincinnati, Ohio) are each mixed with 1 gram of each of the substances as set forth in Table IV of Example XX, supra, until homogeneous compositions are obtained. The homogeneous compositions are each separated then heated under 3 atmospheres pressure at 180° C. for a period of 3 hours and the resulting liquid samples are placed in soap molds. The resulting soap cakes, on cooling, manifest excellent, long lasting aromas as set forth in Table IV of Example XX.

EXAMPLE XXIV

Preparation of Solid Detergent Compositions

Detergents are prepared using the following ingredients according to Example II of Canadian Patent No. 1,007,948, the specification for which is incorporated by reference herein:

| Ingredients | Parts by Weight |
|---|---|
| NEODOL ® 45-11 (a C$_{14}$–C$_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. A total of 100 grams of said detergent is admixed separately with 0.10, 0.15, 0.20 and 0.25 grams of each of the substances as set forth in Table IV of Example XX. Each of the detergent samples has an excellent aroma as set forth in Table IV of Example XX.

EXAMPLE XXV

Dryer-added Fabric Softener Article

Utilizing the procedure of Example II of column 15 of U.S. Pat. No. 3,632,396, the specification for which is incorporated herein by reference, a non-woven cloth substrate useful as a dryer-added fabric softening article of manufacture is prepared wherein the substrate, the substrate coating, the outer coating and the perfuming material are as follows:

1. a water "dissolvable" paper ("Dissolvo Paper");
2. Adogen 448 (m.p. about 140° F.) as the substrate coating; and
3. an outer coating having the following formulation (m.p. about 150° F.):
    57% C$_{20-22}$ HAPS;
    22% isopropyl alcohol;
    20% antistatic agent; and
    1% of one of the perfume materials as set forth in Table IV of Example XX.

Fabric softening compositions containing one of the substances of Table IV of Example XX consist essentially of a substrate having a weight of about 3 grams per 100 square inches of substrate coating having a weight of about 1.85 grams per 100 square inches of substrate; and an outer coating having a weight of about 1.4 grams per 100 square inches of substrate, thereby providing a total aromatized substrate and an outer coating weight ratio of about 1:1 by weight of the substrate. Pleasant aromas as set forth in Table IV of Example XX are imparted to the headspace in the dryer on operation thereof, using the said dryer-added fabric softening, non-woven fabrics.

EXAMPLE XXVI

Three meatloaf-type products are prepared according to the following formulation:

| Ingredients | Amounts |
| --- | --- |
| TVP ® (Note 1) minced | 1 cup |
| Ground beef | 1 cup |
| Water | 1 cup |
| Beef suet | ½ cup |
| Bread crumbs, dry and unflavored | 1 cup |
| Whole milk | 1 cup |
| Egg albumen | 3 tablespoons |
| Salt | 1.25 tablespoons |
| Black pepper | 0.25 tablespoons |
| Catsup | 0.25 tablespoons |
| Water | 32 ml |

(Note 1):
The "TVP ®" is a texturized vegetable protein mixture made by Archer-Daniels-Midland Company.

Three separate portions prepared according to the foregoing formulation are made into three meatloaves. Loaf A contains no additional additive. Loaf B contains 32 ml of fresh pressed onion juice to replace the 32 ml of water. Loaf C contains 0.6 ppm of the mixture of the compound having the structure:

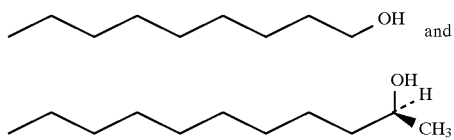

prepared according to Example II and, in addition, 32 ml of fresh pressed onion juice to replace the 32 ml of water.

The three loaves are baked at 350° F. for 1 hour and evaluated for flavor by a panel of twelve judges. The consensus of the judges is that Loaf C is superior to Loaves A and B. The onion/baked goods character of Loaf C enhances the overall taste and covers the dry, cardboard-like cereal character of Loaf A. It is accordingly apparent that the product of this invention is a valuable ingredient for a wide variety of flavors and types of foodstuffs.

What is claimed is:

1. A process for augmenting, enhancing or imparting an aroma in or to a consumable material selected from the group consisting of perfume compositions and perfumed articles comprising the step of intimately admixing with said consumable material an aroma augmenting, enhancing or imparting quantity and concentration of a mixture of compounds having the structures:

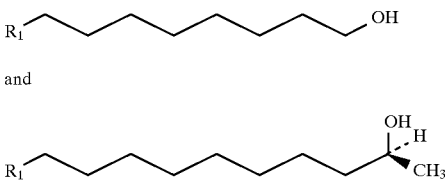

wherein $R_1$ is selected from the group consisting of methyl and n-propyl; and wherein the mixture has an optical rotation of between about +0.2 and about +0.9°.

2. The process of claim 1 wherein $R_1$ is methyl.

3. The process of claim 1 wherein $R_1$ is n-propyl.

4. The process of claim 1 wherein the consumable material is a perfumed article and the perfumed article is selected from the group consisting of detergents, soaps and fabric softener compositions.

5. The process of claim 1 wherein the consumable material is a perfume composition.

* * * * *